US010189865B1

(12) United States Patent
Sulaiman et al.

(10) Patent No.: US 10,189,865 B1
(45) Date of Patent: Jan. 29, 2019

(54) GOLD(I) COMPLEXES, PHARMACEUTICAL COMPOSITIONS THEREOF, AND METHODS OF TREATING PROLIFERATIVE DISORDERS

(71) Applicant: King Fahd University of Petroleum and Minerals, Dhahran (SA)

(72) Inventors: Adam A. A. Sulaiman, Dhahran (SA); Muhammad Altaf, Dhahran (SA); Anvarhusein A. Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/864,650

(22) Filed: Jan. 8, 2018

(51) Int. Cl.
*C07F 1/12* (2006.01)
*A61P 35/00* (2006.01)

(52) U.S. Cl.
CPC ............... *C07F 1/12* (2013.01); *A61P 35/00* (2018.01)

(58) Field of Classification Search
CPC .................................. C07F 1/12; A61P 35/00
See application file for complete search history.

(56) References Cited

PUBLICATIONS

Nahra et al. "Hydrofluorination of Alkynes Catalysed by Gold Bifluorides" ChemCatChem, 2015, vol. 7, pp. 240-244.*
Adam A.A. Seliman, et al., "Synthesis, X-ray structures and anticancer activity of gold(I)-carbene complexes with selonones as co-ligands and their molecular docking studies with thioredoxin reductase", Journal of Organometallic Chemistry, vol. 848, Oct. 15, 2017, pp. 175-183.
Dr. Jens Willwacher, et al., "Total Synthesis, Stereochemical Revision, and Biological Reassessment of Mandelalide A: Chemical Mimicry of Intrafamily Relationships", Chemistry—A European Journal, vol. 21, Issue 29, Jul. 13, 2015, pp. 10416-10430.
David J. Nelson, et al., "Methoxy-Functionalized N-Heterocyclic Carbenes", Organometallics, vol. 33, No. 8, 2014, pp. 2048-2058.
Morgane Gaydou, et al., "Synthesis of (+)-Schisanwilsonene A by Tandem Gold-Catalyzed Cyclization/1,5-Migration/Cyclopropanation", Angewandte Chemie International Edition, vol. 52, Issue 25, Jun. 17, 2013, pp. 6396-6399.
Wontaeck Lim, et al., "A Flexible Metal-Catalyzed Synthesis of Highly Substituted Aryl Phenanthrenyl elenid", European Journal of Organic Chemistry. vol. 2013, Issue 3, Jan. 2013, pp. 460-464.
Adam A. A. Seliman, et al., "Synthesis, X-ray structure, DFT calculations and anticancer activity of a selenourea coordinated gold(I)-carbene complex", Polyhedron. vol. 137, Nov. 24, 2017, pp. 197-206.
Xiangya Xu, et al., "Abnormal N-Heterocyclic Carbene Gold(I) Complexes: Synthesis, Structure, and Catalysis in Hydration of Alkynes", Organometailics, vol. 32, No. 1, 2013, pp. 164-171.
Wukun Liu, et al., "NHC Gold Halide Complexes Derived from 4,5-Diarylimidazoles: Synthesis, Structural Analysis, and Pharmacological Investigations as Potential Antitumor Agents", Journal of Medical Chemistry, vol. 54, No. 24, 2011, pp. 8605-8615.
Louis Ricard, et al., "Synthesis and Reactivity of Air-Stable N-Heterocyclic Carbene Gold(I) Bis(trifluoromethanesulfonyl)imidate Complexes", Organometallics, vol. 26, No. 19, 2007, pp. 4704-4707.
Luigi Messori, et al., "Chemistry and Biology of Two Novel Gold (I) Carbene Complexes as Prospective Anticancer Agents", Inorganic Chemistry, vol. 53, No. 5, 2014, pp. 2396-2403.

* cited by examiner

*Primary Examiner* — Joseph R Kosack
(74) *Attorney, Agent, or Firm* — Oblon, McClelland, Maier & Neustadt, L.L.P.

(57) ABSTRACT

Gold(I) complexes as antiproliferative or antitumor agents. The gold(I) ion is connected to a N-heterocyclic carbene and further coordinated to a selone ligand. Also described are a pharmaceutical composition incorporating the gold(I) complex, a method of synthesizing the gold(I) complex, and a method for treating a proliferative disorder (e.g. cancer)

20 Claims, 9 Drawing Sheets

Carbon-Grey, Gold-Yellow, Selenium-Pink, Hydrogen-White

GOLD(I) COMPLEXES, PHARMACEUTICAL COMPOSITIONS THEREOF, AND METHODS OF TREATING PROLIFERATIVE DISORDERS

STATEMENT OF FUNDING ACKNOWLEDGEMENT

This project was funded by King Fahd University of Petroleum and Minerals (KFUPM) under the project number IN151022.

STATEMENT REGARDING PRIOR DISCLOSURE BY THE INVENTORS

Aspects of this technology are described in an article "Synthesis, X-ray Structures and Anticancer Activity of Gold(I)-carbene Complexes with Selenones as Co-ligands and Their Molecular Docking Studies with Thioredoxin Reductase" published in Journal of Organometallic Chemistry, 2017, 848, 175-183, on Jul. 29, 2017, which is incorporated herein by reference in its entirety.

BACKGROUND OF THE INVENTION

Technical Field

The present disclosure relates to gold(I) complexes with antiproliferative or antitumor activities. More specifically, these gold(I) complexes are gold(I)-carbenes having selones as co-ligands.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Gold(I) compounds have been used for treatment of rheumatoid arthritis since the 1930s (J. Forestier, *J. Lab. Clin. Med.*, 1935, 20, 827-840; and S. P. Fricker, *Gold bulletin.*, 1996, 29, 53-60). Clinically prescribed anti-arthritis gold(I) complexes include gold(I) thiomalate (Myocrisin), gold(I) thioglucose (Solganol), and (2,3,4,6-tetra-O-acetyl-1-(thio-kS)-b-D-glucopyranosato)-(triethylphosphine)gold(I) (Auranofin) (C. F. Shaw III, *Chem. Rev.*, 1999, 99, 2589-600; and S. Ahmad, A. A. Isab, S. Ali and A. R. Al-Arfaj, *Polyhedron,* 2006, 25, 1633-1645). In addition to anti-arthritic properties, some gold(I) complexes have demonstrated anticancer activities (M. Altaf, M. Monim-ul-Mehboob , M. Ogasawara , N. Casagrande, M. Celegato, C. Borghese, Z. H. Siddik, D. Aldinucci, A. A. Isab, *Oncotarget,* 2017, 8, 490-505; S.-H. G. Park, J. H. Lee, J. S. Berek and M. C.-T. Hu, *Int. J. Oncol.,* 2014, 45, 1691-1698; K. K. Ooi, C. I. Yeo, K. P. Ang, A. M. Akita, Y. K. Cheah, S. N. A. Halim, H. L. Seng and E. R. T. Tiekink, *J. Biol. Inorg. Chem.,* 2015, 20, 855-873; M. Ali, L. Dondaine, A. Adolle, C. Sampaio, F. Chotard, P. Richard, F. Denat, A. Bettaieb, P. Le Gendre, V. Laurens, C. Goze, C. Paul and E. Bodio, *J. Med. Chem.,* 2015, 58, 4521-4528; J. D. Chaves, F. Neumann, T. M. Francisco, C. C. Correa, M. T. P. Lopes, H. Silva, A. P. S. Fontes and M. V. Almeida, *Inorg. Chim. Acta,* 2014, 414, 85-90; and A. A. A. Sulaiman, M. Altaf, A. A. Isab, A. Alawad, S. Altuwaijri and S. Ahmad, *Z. Anorg. Allg. Chem.,* 2016, 642, 1454-1459, each incorporated herein by reference in their entirety). A good example is auranofin, which has undergone clinical trials for treatment of several types of cancer (W. Fiskus, N. Saba, M. Shen, M. Ghias, J. Liu, S. D. Gupta, L. Chauhan, R. Rao, S. Gunewardena, K. Schorno, C. P. Austin, K. Maddocks, J. Byrd, A. Melnick, P. Huang, A. Wiestner and K. N. Bhalla, *Cancer Res.,* 2014, 74, 2520-2532; and X. Chen, X. Shi, C. Zhao, X. Li, X. Lan, S. Liu, H. Huang, N. Liu, S. Liao, D. Zang. W. Song, Q. Liu, B. Z. Carter, Q. P. Dou and X. Wang, J. I. *Oncotarget,* 2014, 5, 9118-9132, each incorporated herein by reference in their entirety). Furthermore, gold(I) complexes of N-heterocyclic carbenes (NHCs), especially gold(I)-NHCs derived from imidazolium and benzimidazolium salts, have been investigated in recent years (B. Bertrand and A. Casini, *Dalton Trans.,* 2014, 43, 4209-4219; J. Weaver, S. Gaillard, C. Toye, S. Macpherson, S. P. Nolan and A. Riches, *Chem. Eur. J.,* 2011, 17, 6620-6624; B. Bertrand, A. Citta, I. L. Franken, M. Picquet, A. Folda, V. Scalcon, M. P. Rigobello, P. Le Gendre, A. Casini and E. Bodio, *J. Biol. Inorg. Chem.,* 2015, 20, 1005-1020; A. Pratesi, D. Cirri, M. D. Duovic, S. Pillozzi, G. Petroni, Z. D. Bugarcic and L. Messori, *Biometals,* 2016, 29, 905-911; L. Messori, L. Marchetti, L. Massai, F. Scaletti, A. Guerri, I. Landini, S. Nobili, G. Perrone, E. Mini, P. Leoni, M. Pasquali, and C. Gabbiani, *Inorg. Chem.,* 2014, 53, 2396-2403; S. Gaillard, A. M. Z. Slawin and S. P. Nolan, *Chem. Commun.,* 2010, 46, 2742-2744; O. Schuster, L. Yang, H. G. Raubenheimer and M. Albrecht, *Chem. Rev.,* 2009, 109, 3445-3478; and X. Xu, S. H. Kim, X. Zhang, A. K. Das, H. Hirao and S. H. Hong, *Organometallics,* 2013, 32, 164-171, each incorporated herein by reference in their entirety). Due to their ability to form strong coordinate covalent bonds through σ-donation, carbene ligands form stable gold complexes (D. Marchione, L. Belpassi, G. Bistoni, A. Macchioni, F. Tarantelli and D. Zuccaccia, *Organometallics,* 2014, 33, 4200-4208; D. Benitez. N. D. Shapiro, E. Tkatchouk, Y. Wang, W. A. Goddard and F. D. Toste, *Nature Chem.,* 2009, 1, 482-486; and L. N. D. S. Comprido, J. E. M. N. Klein, G. Knizia, J. Kastner and A. S. K. Hashmi, *Angew. Chem, Int. Ed.,* 2015, 54, 10336-10340, each incorporated herein by reference in their entirety). Despite these recent advances, there remains a need to develop more efficient gold(I) anticancer agents.

In view of the forgoing, it is one objective of present disclosure to provide a therapeutic gold(I) complex with N-heterocyclic carbene and heterocyclic selone co-ligands and a method for treating cancer.

BRIEF SUMMARY OF THE INVENTION

According to a first aspect, the current disclosure relates to a gold(I) complex of Formula (I)

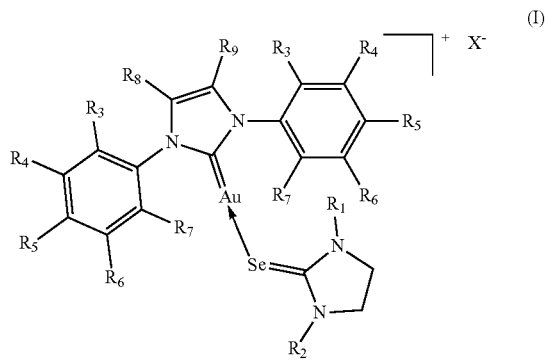

or a salt thereof, a solvate thereof, a tautomer thereof, a stereoisomer thereof, or a mixture thereof,
where (i) $R_1$ and $R_2$ are independently selected from the group consisting of a hydrogen, an optionally substituted alkyl, an optionally substituted cycloalkyl an optionally substituted aryl, and an optionally substituted arylalkyl, (ii) $R_3$, $R_4$, $R_5$, $R_6$, and $R_7$ are independently selected from the group consisting of a hydrogen, an optionally substituted alkyl, an optionally substituted alkenyl, an optionally substituted alkynyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro, (iii) $R_8$ and $R_9$ are independently a hydrogen, or an optionally substituted alkyl, and (iv) X is an anion.

In one embodiment, the anion is a hexafluorophosphate ion, a trifluoromethanesulfonate ion, a tetrafluoroborate ion, a perchlorate ion, or a halide ion.

In one embodiment, $R_1$ and $R_2$ are independently a hydrogen or an optionally substituted $C_1$-$C_6$ alkyl, $R_3$ and $R_7$ are an isopropyl, $R_4$, $R_5$, $R_6$, $R_8$, and $R_9$ are a hydrogen, and X is a hexafluorophosphate.

In one embodiment, $R_1$ and $R_2$ are independently selected from the group consisting of a hydrogen, a methyl, an ethyl, and a n-propyl.

In one embodiment, the gold(I) complex is a compound selected from the group consisting of

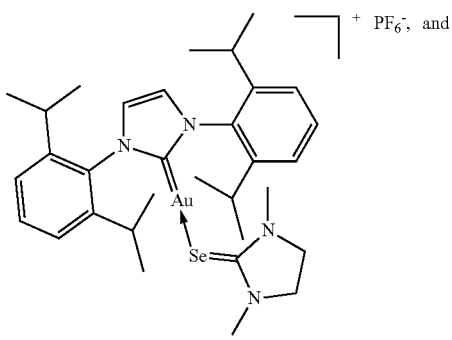

(II), (III), (IV)

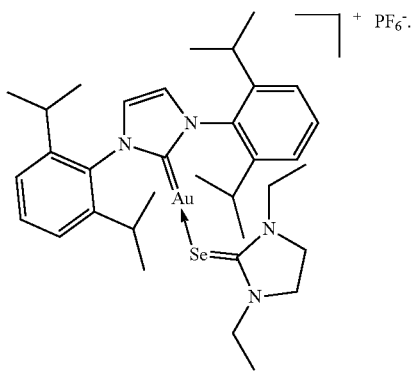

(V), and (VI)

According, to a second aspect, the current disclosure relates to a pharmaceutical composition including the gold (I) complex of Formula (I) of the first aspect, and a pharmaceutically acceptable carrier and/or excipient.

In one embodiment, the pharmaceutical composition contains 0.1-400 µM of the gold(I) complex relative to the total volume of the composition.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In one embodiment, the pharmaceutical composition further includes to chemotherapeutic agent.

In one embodiment, $R_1$ and $R_2$ are independently selected from the group consisting of a hydrogen, a methyl, an ethyl, and a n-propyl, $R_3$ and $R_7$ are an isopropyl, $R_4$, $R_5$, $R_6$, $R_8$, and $R_9$ are a hydrogen, and X is a hexafluorophosphate.

In one embodiment, the gold(I) complex is (II)

or a salt thereof, a solvate thereof, or a mixture thereof.

According to a third aspect, the current disclosure relates to a method for treating a proliferative disorder, comprising administering the pharmaceutical composition of the second aspect to a subject in need of therapy.

In one embodiment, 1-300 mg/kg of the gold(I) complex of Formula (I) is administered per body weight of the subject.

In one embodiment, $R_1$ and $R_2$ are independently selected from the group consisting of a hydrogen, a methyl, an ethyl, and a n-propyl, $R_3$ and $R_7$ are an isopropyl, $R_4$, $R_5$, $R_6$, $R_8$, and $R_9$ are a hydrogen, and X is a hexafluorophosphate.

In one embodiment, the proliferative disorder is cancer.

In one embodiment, the cancer is at least one selected from the group consisting of colon cancer, breast cancer, and lung cancer.

In one embodiment, the cancer is resistant to at least one platinum-based chemotherapy drug.

In one embodiment, the cancer is colon cancer.

In one embodiment, the platinum-based chemotherapy drug is cisplatin.

In one embodiment, the subject is a mammal.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
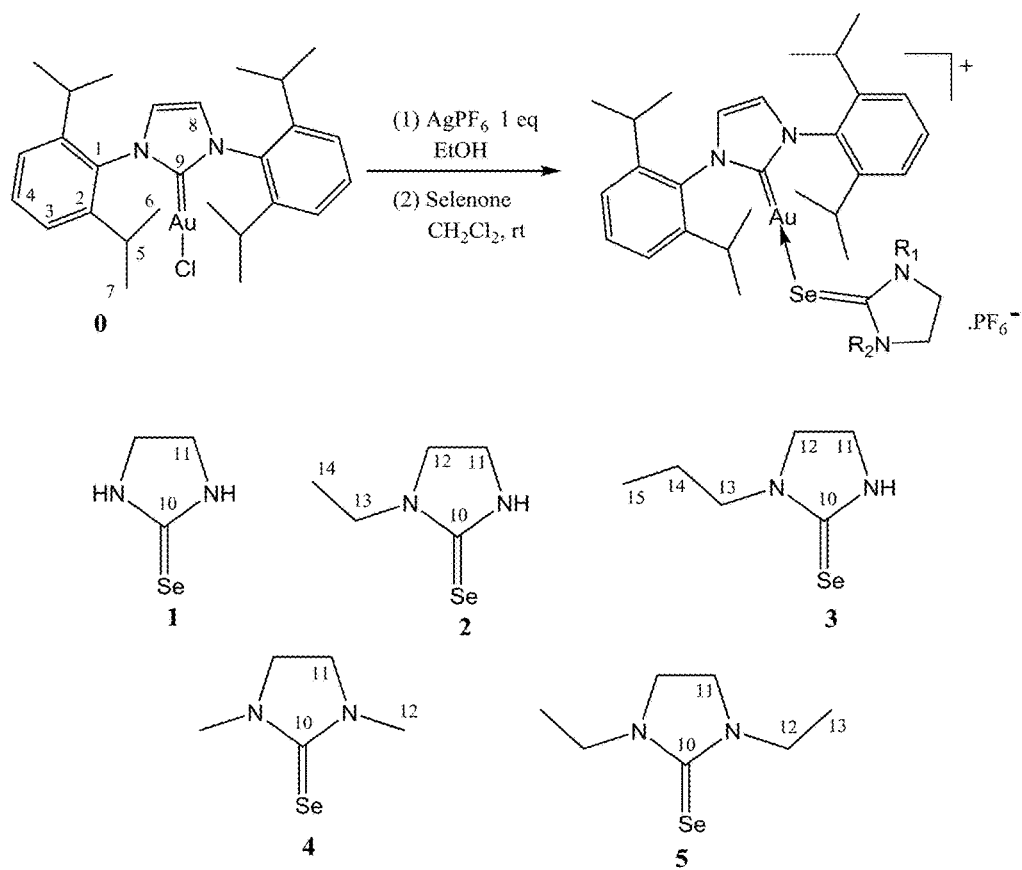
FIG. 1 is a synthetic procedure for gold(I) complexes (II)-(VI) using precursor complex 0, and selenone ligands 1-5.

Embodiments of the present disclosure will now be described more fully hereinafter with reference to the accompanying drawings, in which some, but not all embodiments of the disclosure are shown.

As used herein, the terms "compound" and "complex" are used interchangeably, and are intended to refer to a chemical entity, whether in a solid, liquid or gaseous phase, and whether in a crude mixture or purified and isolated.

Unless otherwise specified "a" or "an" means "one or more".

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, organic solvents, e.g. alcohols such as methanol, ethanol, trifluoroethanol, n-propanol, i-propanol, n-butanol, i-butanol, t-butanol, n-pentanol, i-pentanol, 2-methyl-2-butanol, 2- trifluoromethyl-2-propanol, 2,3-dimethyl-2-butanol,3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, and cyclohexanol, amide solvents such as dimethylformamide (DMF), dimethylacetamide (DMA), and N-methyl-2-pyrrolidone (NMP), aromatic solvents such as benzene, o-xylene, m-xylene, p-xylene, and mixtures of xylenes, toluene, mesitylene. anisole, 1,2-dimethoxybenzene, α,α,α-trifluoromethylbenzene, and fluorobenzene, chlorinated solvents such as chlorobenzene, dichloromethane (DCM), -dichloroethane, 1,1-dichloroethane, and chloroform, ester solvents such as ethyl acetate, and propyl acetate, ethers such as diethyl ether, tetrahydrofuran (THF), 1,4-dioxane, tetrahydropyran, t-butyl methyl ether, cyclopentyl methyl ether, and di-isopropyl ether, glycol ethers such as 1,2-dimethoxyethane, diglyme, and triglyme, acetonitrile, propionitrile, butyronitrile, benzonitrile, dimethyl sulfoxide (DMSO), water, e.g. tap water, distilled water, doubly distilled water, deionized water, and deionized distilled water, and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is, possible, a chemical equilibrium of the tautomers will be reached. The exact ratio of the tautomers depends on several factors including, but not limited to, temperature, solvent and pH. Exemplary common tautomeric pairs include, but are not limited to. ketone and enol, enamine and imine, ketene and ynol, nitroso and oxime, amide and imidic acid, lactam and lactim (an amide and imidic tautomerism in heterocyclic rings), enamine and enamine and anomers of reducing sugars.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In teens of the present disclosure, stereoisomers may refer to enantiomers. diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, isotopes of selenium include $^{74}Se$, $^{76}Se$, $^{77}Se$, $^{78}Se$, and $^{80}Se$, and isotopes of oxygen include $^{16}O$, $^{17}O$, and $^{18}O$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the current disclosure relates to a gold(I) complex of Formula (I)

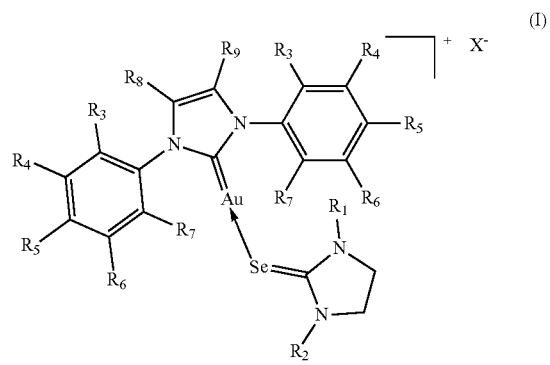

or a salt thereof a solvate thereof, a tautomer thereof, a stereoisomer thereof, or a mixture thereof, where (i) $R_1$ and $R_2$ are independently selected from the group consisting of a hydrogen, an optionally substituted alkyl, an optionally substituted cycloalkyl an optionally substituted aryl, and an optionally substituted arylalkyl, (ii) $R_3$, $R_4$, $R_5$, $R_6$, and $R_7$ are independently selected from the group consisting of a hydrogen, an optionally substituted alkyl, an optionally substituted alkenyl, an optionally substituted alkynyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro, (iii) $R_8$ and $R_9$ are independently a hydrogen, or an optionally substituted alkyl, and (iv) X is an anion.

As used herein, gold(I) describes gold in an oxidation state of +1. One example of a gold(I) compound is gold(I) chloride with a formula AuCl. In contrast, gold(III) refers to gold in an oxidation state of +3, such as gold(III) fluoride with a formula $AuF_3$.

As used herein, an N-heterocyclic carbene or NHC is a cyclic ligand containing a carbene with the simplest structure of Formula (VII)

An NHC may form a robust metal-carbene bond with a majority of transition metals such as gold and palladium and yield a stable metal-complexed NHC. In a preferred embodiment, the NHC in the current disclosure has a structure of Formula (VIII)

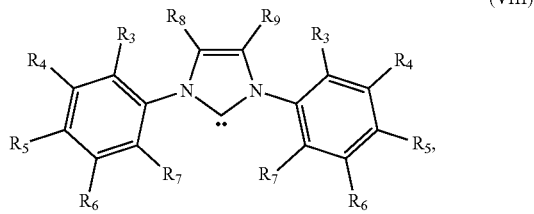

(VIII)

in which $R_3$, $R_4$, $R_5$, $R_6$, and $R_7$ are independently selected from the group consisting of a hydrogen, an optionally substituted alkyl, an optionally substituted alkenyl, an optionally substituted alkynyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro, and $R_8$ and $R_9$ are independently a hydrogen, or an optionally substituted alkyl. Most preferably, $R_3$ and $R_7$ are an isopropyl, and $R_4$, $R_5$, $R_6$, $R_8$, and $R_9$ are a hydrogen.

A selone or a selenone used herein refers to any carbonyl compound where the carbonyl oxygen is replaced by selenium. As a more specific class of selone, a selenourea is an organoselenium compound having a carbon-selenium double bond with the simplest formula $SeC(NH_2)_2$. It is often used as a precursor in the synthesis of selenium-containing heterocycles, which may exhibit potential anti-inflammatory and/or antitumor activities. As a result of its electron-donating amino groups, selenourea can also act as an effective ligand for complexation with transition metals. The binding of a soft selenium ligand to gold(I) trans to its carbene ligand could induce further stability to the resulting complexes (S. Ahmad, M. N. Akhtar, A. A. Isab, A. R. Al-Arfaj and M. S. Hussain, *J. Coord. Chem.*, 2000, 51, 225-234, incorporated herein by reference in its entirety).

In a preferred embodiment, the selone in the current disclosure has a heterocyclic imidazolidine-based structure of Formula (IX)

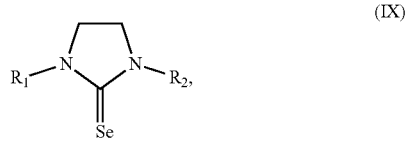

(IX)

in which $R_1$ and $R^2$ are independently selected from the group consisting of a hydrogen, an optionally substituted alkyl, an optionally substituted cycloalkyl, an optionally substituted aryl, and an optionally substituted arylalkyl.

As shown in Formula (I), a gold(I) central atom is bound to an NHC of Formula (VIII), while a selone ligand of Formula (IX) is coordinated to the gold(I) via a Se—Au bond. The arrow "→" used herein may represent a coordinate covalent bond, or a dative bond, and indicate a direction of the shift in electron density, e.g. from the selone ligand to the gold(I).

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl. or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{10}$, preferably $C_1$ to $C_6$. more preferably $C_2$ to $C_3$, and specifically includes, but is not limited to, methyl, trifluoromethyl, ethyl, n-propyl, isopropyl, n-butyl, sec-butyl, isobutyl, t-butyl, pentyl, isopentyl, neopentyl, hexyl, isohexyl, 3-methylpentyl, 2,2-dimethylbutyl, and 2,3-dimethylbutyl.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "alkynyl" refers to a straight or branched hydrocarbon fragment containing at least one C≡C triple bond. Exemplary alkynyl groups include, without limitation, ethynyl, 1-propynyl, 2-propynyl (i.e., propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, and 9-decynyl.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

As used herein, the term "aryl" unless otherwise specified refers to functional groups or substituents derived from an aromatic ring including, but not limited to, phenyl, biphenyl, napthyl, anthracenyl, thienyl, and indolyl.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkanoyl", as used herein, refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluoro, chloro, bromo and iodo.

The term "anion" means a negatively charged ion including, but not limited to, halides, such as fluoride, chloride, bromide, and iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, tetrafluoroborate, hexafluorophosphate, and hexafluoroacetylacetonate. In one or more embodiments, the anion X of gold(I) complex of Formula (I) is a hexafluorophosphate ion, a trifluoromethanesulfonate ion, a tetrafluoroborate ion, a perchlorate ion, or a halide ion.

In one or more embodiments, $R_1$ and $R_2$ are independently a hydrogen or an optionally substituted $C_1$-$C_6$ alkyl, $R_3$ and $R_7$ are an isopropyl, $R_4$, $R_5$, $R_6$, $R_8$, and $R_9$ are a hydrogen, and anion X is a hexafluorophosphate. In one or more embodiments, $R_1$ and $R_2$ are the same. In one or more embodiments, $R_1$ and $R_2$ are different.

In one or more embodiments, $R_1$ and $R_2$ are independently selected from the group consisting of a hydrogen, a methyl, an ethyl, and a n-propyl.

In one or more embodiments, the gold(I) complex is a compound selected from the group consisting of

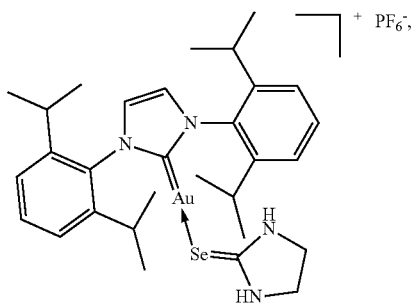

(II)

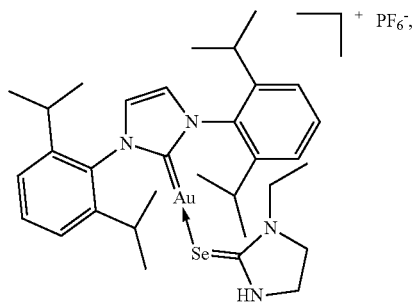

(III)

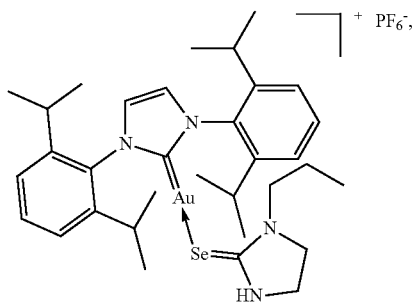

(IV)

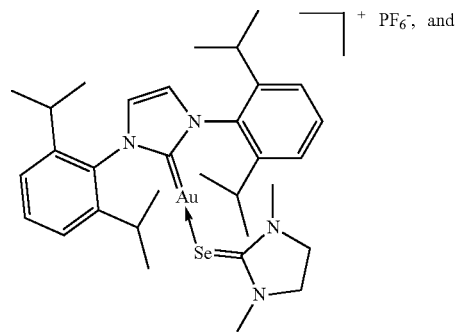

(V)

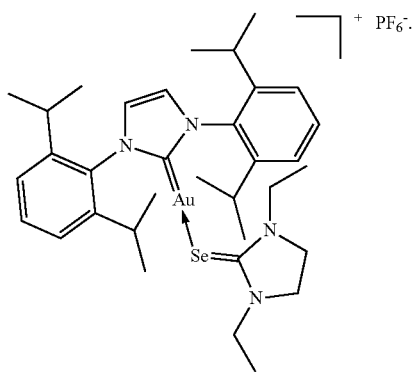

(VI)

In one or more embodiments, the gold(I) complex of the first aspect can be prepared by reacting a gold-NHC compound of Formula (X)

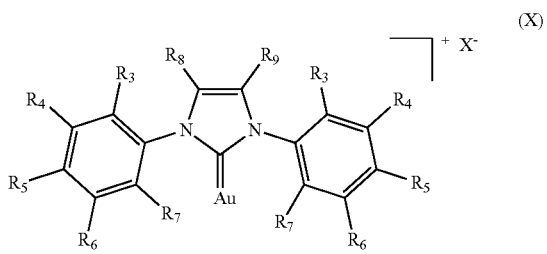

(X)

with a selone ligand of Formula (IX), wherein $R_3$, $R_4$, $R_5$, $R_6$, and $R_7$ are independently selected from the group consisting of a hydrogen, an optionally substituted alkyl, an optionally substituted alkenyl, an optionally substituted alkynyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro, $R_8$ and $R_9$ are independently a hydrogen, or an optionally substituted alkyl, and X is an anion. The gold-NHC compound of Formula (X) may be dissolved in a solvent to give a solution with a concentration in a range of 0.001-0.5 M, preferably 0.02-0.25 M, more preferably 0.03-0.1 M. The selone of Formula (IX) may be added to the solution to form a reaction mixture with a molar ratio in a range of 0.9:1 to 1.5:1, 0.95:1 to 1.2:1, or 0.98:1 to 1.1:1, or about 1:1 relative to the gold-NHC compound. The reaction mixture may be agitated for 0.1-12 hours, 0.5-6 hours, or 1-3 hours. Preferably, the solvent is dichloromethane.

The reaction mixture may then be filtered to collect a second solution. The second solution may be concentrated by evaporating a solvent to yield a crude gold(I) complex of Formula (I). The crude gold(I) complex of Formula (I) may be further purified by methods known to those skilled in the art, for example, aqueous workup, extraction with solvents, distillation, recrystallization, column chromatography, and high-performance liquid chromatography (HPLC). Precipitation/crystallization of the gold(I) complex may occur, and the precipitate/crystals may be collected using methods known to those skilled in the art such as filtration. In one or more embodiments, the yield of the gold(I) complex is at least 40%, preferably at least 50%, preferably at least 55%, preferably at least 60%, preferably at least 70%, preferably at least 80% by weight.

Methods of agitating a reaction mixture include, without limitation, using an agitator, a vortexer, a rotary shaker, a magnetic stirrer, a centrifugal mixer, or an overhead stirrer. In one embodiment, the mixture is mixed with a spatula. In another embodiment, the mixture is agitated by sonication in an ultrasonic bath or with an ultrasonic probe. In another embodiment, the mixture is left to stand without being stirred. In a preferred embodiment, the mixture is agitated using a magnetic stirrer with a rotational speed of at least 250 rpm, preferably at least 400 rpm, more preferably at least 600 rpm.

According to a second aspect, the current disclosure relates to a pharmaceutical composition including the gold (I) complex of Formula (I) of the first aspect, and a pharmaceutically acceptable carrier and/or excipient.

In one or more embodiments, $R_1$ and $R_2$ of the gold(I) complex of Formula (I) are independently selected from the group consisting of a hydrogen, a methyl, an ethyl, and a n-propyl, $R_3$ and $R_7$ are an isopropyl, $R_4$, $R_5$, $R_6$, $R_8$, and $R_9$ are a hydrogen, and X is a hexafluorophosphate.

In one embodiment, the pharmaceutical composition comprises gold(I) complex

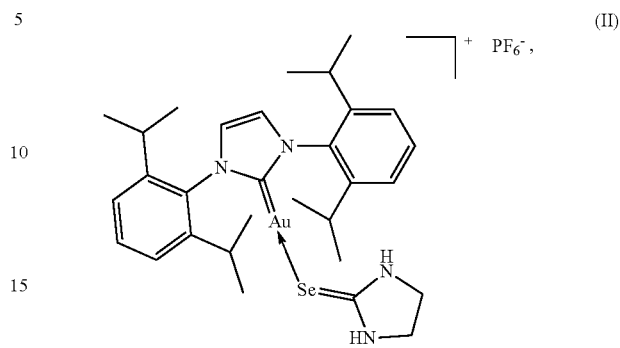

(II)

or a salt thereof, a solvate thereof or a mixture thereof.

As used herein, a "composition" or a "pharmaceutical composition" refers to a mixture of the active ingredient with other chemical components, such as pharmaceutically acceptable carriers and excipients. One purpose of a composition is to facilitate administration of the gold(I) complex to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the gold(I) complex represented by Formula (I), a salt thereof, a solvate thereof, a tautomer thereof, a stereoisomer thereof, or any mixtures thereof.

In one or more embodiments, the pharmaceutical composition comprises at least 0.01 wt %, 0.05 wt %, 0.1 wt %, 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt % of the gold(I) complex of Formula (I) relative to the total weight of the composition. The pharmaceutical composition may contain 0.1-400 µM, 1-300 µM, preferably 10-200 µM of the gold(I) complex relative to the total volume of the composition. In some embodiments, the composition comprises up to 0.1 wt %, 1 wt %, 5 wt %, or 10 wt % of a pharmaceutically acceptable salt of the gold(I) complex of Formula (I). In some embodiments, the composition comprises up to 0.1 wt %, 1 wt %, 5 wt %, or 10 wt % of a pharmaceutically acceptable solvate of the gold(I) complex of Formula (I). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

Previous studies on mechanisms of the anticancer action of gold(I) complexes have shown that they mainly act as inhibitors of mitochondrial enzymes including thioredoxin reductase (TrxR) (Y. Li, G.-F. Liu, C.-P. Tan, L.-N. Ji and Z.-W. Mao, Metallomics, 2014, 6, 1460-1468; P. J. Barnard, M. V. Baker, S. J. Berners-Price and A. D. Day, *J. Inorg.*

Biochem., 2004, 98, 1642-1647; R. Rubbiani, E. Schuh, A. Meyer, J. Lemke, J. Wimberg, N. Metzler-Nolte, F. Meyer, F. Mohr and. I. Ott, *Med. Chem. Commun.*, 2013, 4, 942-948; E. Schuh, C. Pfluger, A. Citta, A. Folda, M. P. Rigobello, A. Bindoli, A. Casini, and F. Mohr, *J. Med. Chem.*, 2012, 55, 5518-5528; and M. V. Baker, P. J. Barnard, S. J. Berners-Price, S. K. Brayshaw, J. L. Hickley, B. W. Skelton and A. H. White, *Dalton Trans.*, 2006, 3708-3715, each incorporated herein by reference in their entirety). Inhibition of TrxR may lead to the generation of oxidized forms of Trx and Prx III (Peroxiredoxin 3) and reactive oxygen species (ROS). The elevation of ROS level in cancer cells causes oxidative stress in them, thus induces cancer cell apoptosis (J. L. Hickey, R. A. Ruhayel, P. J. Barnard, M. V. Baker, S. J. Berners-Price and A. Filipovska, *J. Am. Chem. Soc.*, 2008, 130, 12570-12571; X. Cheng, P. Holenya, S. Can, H. Alborzinia, R. Rubbiani, I. Ott and S. Wolfl, *Mol. Cancer*, 2014, 13, 221; and A. Citta, E. Schuh, F. Mohr, A. Folda, M. Massimino, A. Bindoli, A. Casini and M. P. Rigobello, *Metallomics*, 2013, 5,1006-1015, each incorporated herein by reference in their entirety).

In some embodiments, the ability of the active ingredient to reduce the viability of cancer cells may be determined by contacting the pharmaceutical composition with the cancer cells and then performing cell viability assays. Methods of such assays include, without limitation, ATP test, Calcerin AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GP5d, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA, HR5, and C-4I, ovarian cancer cell lines, e.g., A2780, A2780cis, OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably colon cancer, lung cancer, and/or breast cancer. In at least one embodiment, cisplatin-resistant cancer cells are used. These cells may be generated by culturing cancer cells with low doses of cisplatin in order to build their resistance to cisplatin while maintaining cell viability. Examples of cisplatin-resistant cancer cells include, but are not limited to, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

As used herein, the term "cytotoxic effective amount" refers to a concentration of the active ingredient that reduces the viability of the cancer cells by at least 5%, 10%, 15%, 20%, 30%, 40%, 50%, 60%, 70%, 80% or 90%, relative to cancer cells not treated with the active ingredient. The reduction in viability may occur no more than 10 days, 7 days, 5 days, 3 days, or 2 days after the active ingredient is contacted with the cancer cells. In one embodiment, the cytotoxic effective amount may be the $IC_{50}$ which is a concentration of the active ingredient which causes the death of 50% of cancer cells in 72 hours (3 days). In one embodiment, the $IC_{50}$ of the gold(I) complex of Formula (I), the salt thereof, the solvate thereof, the tautomer thereof, the stereoisomer thereof, or the mixture thereof against colon cancer cells is in a range of 0.01-150 µM, preferably 1-70 µM, more preferably 30-40 µM. In another embodiment, the $IC_{50}$ of the gold(I) complex of Formula (I), the salt thereof, the solvate thereof, the tautomer thereof, the stereoisomer thereof, or the mixture thereof against lung cancer cells is in a range of 0.01-200 µM, preferably 1-80 µM, more preferably 40-50 µM. In another embodiment, the $IC_{50}$ of the gold(I) complex of Formula (I), the salt thereof, the solvate thereof, the tautomer thereof, the stereoisomer thereof, or the mixture thereof against breast cancer cells is in a range of 0.01-120 µM. preferably 1-60 µM, more preferably 40-50 µM.

In some embodiments, other active ingredients in addition to the gold(I) complex of the current disclosure may be incorporated into a pharmaceutical composition. In one embodiment, the pharmaceutical composition includes a second active ingredient, such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis, and benign proliferative breast disease such as ductal hyperplasia, lobular hyperplasia, and papillomas.

The anticancer agent is at least one of a mitotic inhibitor; an alkylating agent; an antimetabolite; a cell cycle inhibitor; an enzyme; a topoisomerase inhibitor: a biological response modifier; an anti-hormone; an antiangiogenic agent such as MMP-2, MMP-9 and COX-2 inhibitor; an anti-androgen; a platinum coordination complex (oxaliplatin, carboplatin): a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol): an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti- microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid. eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation. methyl, ethyl. isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$, fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g.. phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage form such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition having the gold(I) complex of Formula (I), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in, dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

According to a third aspect, the current disclosure relates to a method for treating a proliferative disorder, comprising administering the pharmaceutical composition of the second aspect to a subject in need of therapy.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5% preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the third aspect is for treating cancer of the blood, brain, bladder, liver, cervix, ovary, colon, rectum, pancreas, skin, prostate gland, stomach, breast, spleen, liver, kidney, head, neck, testicle, bone, bone marrow, thyroid gland, or central nervous system. In a preferred embodiment, the cancer is at least one selected from the group consisting of colon cancer, breast cancer, and lung cancer. In a more preferred embodiment, the cancer is colon cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens such as asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

In another embodiment, the subject refers to a cancer patient who has been previously administered and/or treated with a platinum-based chemotherapy drug such as Carboplatin, Oxaliplatin, Nedaplatin, Phenanthriplatin, Picoplatin, Satraplatin, Lipoplatin, and cisplatin, and developed resistance to the drug. In some embodiments, the subject refers to a cancer patient who has been previously treated and/or administered with cisplatin and develops cisplatin resistance due to reduced intracellular drug accumulation, overexpression of HER-2/neu and the PI3-K/Akt pathway, increase in DNA damage repair, dysfunction of tumor-suppressor p53, loss of pAMT function, and/or overexpression of antiapoptotic bcl-2. In at least one embodiment, the subject has colon, breast, and/or lung cancer and is currently undergoing, or has completed a cisplatin-based chemotherapy regimen.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can he employed with the compounds and methods described herein. In preferred embodiments, the active ingredient and/or the composition described herein are administered orally.

In one or more embodiments, the pharmaceutical composition administered comprises the gold(I) complex of Formula (I), or a salt thereof, a solvate thereof, a tautomer thereof, a stereoisomer thereof, or a mixture thereof, in which $R_1$ and $R_2$ are independently selected from the group consisting of a hydrogen, a methyl, an ethyl, and a n-propyl, $R_3$ and $R_7$ are an isopropyl, $R_4$, $R_5$, $R_6$, $R_8$, and $R_9$ are a hydrogen, and X is a hexafluorophosphate. In a preferred embodiment, the pharmaceutical composition administered comprises the gold(I) complex of Formula (II)

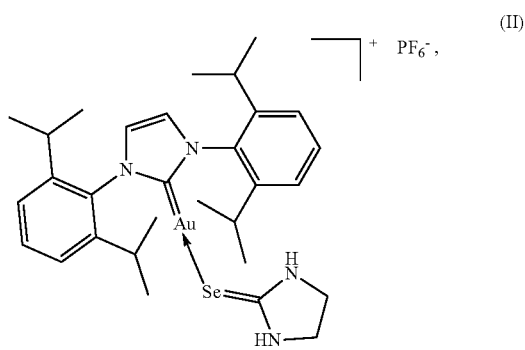

(II)

or a salt thereof, a solvate thereof, or a mixture thereof.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount of the gold(I) complex of Formula (I) in a range of 1-300 mg/kg, preferably 10-200 mg/kg, more preferably 50-100 mg/kg is administered per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition containing the gold(I) complex of the current disclosure as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments, the method further comprises measuring a concentration of a biomarker and/or detecting a mutation in a biomarker before and/or after the pharmaceutical composition comprising the gold(I) complex of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Exemplary biomarkers for lung cancer include, without limitation, CA 125, CA 15-3, EGF receptor, anaplastic lymphoma kinase gene, MET, ROS-1, and KRAS. Potentially predictive cancer biomarkers include, without limitation, mutations in genes BRCA1 and BRCA2 for breast cancer and/or ovarian cancer, overexpressions of CEA, NSE, CYFRA-21-1, CA-125, and CA-199 for lung cancer, overexpressions of TYMS, mutations in genes p53 and KRAS for colon cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the gold(I) complex by at least 5%, at least 10%, or at least 30%, up to 50%, up to 60%, or up to 80% of an initial effective amount that is in a range of 1-300 mg/kg per body weight of the subject. The increased effective amount may be in a range of 1.05-540 mg/kg, preferably 15-420 mg/kg, more preferably 25-270 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Having generally described this disclosure, a further understanding can be obtained by reference to certain specific examples which are provided herein for purposes of illustration only and are not intended to be limiting unless otherwise specified.

EXAMPLE 1

Chemicals 1,3-bis(2,6-di-isopropylphenyl)imidazol-2-ylidenegold(I) chloride ([Au(Ipr)Cl], complex 0) and AgPF$_6$ were purchased from Sigma-Aldrich Company, St. Louis, Mo., USA. ImSe (ligand 1) and its derivatives (ligands 2-5) were synthesized according to methods reported in the literature (M. I. M. Wazeer, A. A. Isab and H. P. Perzanowski, *Magn. Reson. Chem.*, 2003, 41, 1026-1029; and F. A. Devillanova and G. Verani, *Spectrochim. Acta Part A Mol. Spectrosc.*, 1980, 36, 371-373, each incorporated herein by reference in their entirety). Human colon cancer, human breast cancer and human lung cancer cell lines were purchased from National Centre for Cell Sciences (NCCS), Pune India.

EXAMPLE 2

Instrumentation

Elemental analysis was performed on Perkin Elmer Series 11(CHNS/O), Analyzer 2400. The solid state FTIR spectra were recorded on a Perkin Elmer FTIR 180 spectrophotometer using KBr pellets over the range 4000-400 cm$^{-1}$ at a resolution 4 cm$^{-1}$. The $^1$H (500.01 MHz), $^{13}$C (125.65 MHz) and $^{77}$Se (200.0 MHz) NMR spectra were recorded on a LAMBDA 500 MHz N MR spectrometer. The $^1$H and $^{13}$C chemical shifts were referenced with respect to tetramethylsilane (TMS), while for $^{77}$Se NMR, NaHSeO$_3$ (1308 ppm) was used as an external standard. The $^{13}$C (MAS) NMR results were recorded on a Bruker 400.0 MHz spectrometer at the ambient room temperature of 298 K. Samples were packed into 4 mm zirconium oxide rotors. Pulse delay of 7.0 s and a contact time of 5.0 ms. The magic angle spinning rates were 4 and 8 kHz. $^{13}$C chemical shifts were measured relative to adamantine, which resonates at 38.56 ppm.

The X-ray data for complexes (III) and (V) were collected at 173 K on a STOE IPSD II Image Plate Diffraction System connected with a two-circle goniometer using a MoKα graphite monochromator (λ=0.71073 Π). Structures were solved by SHELXS-2014 program (G. M. Sheldrick, A short, of SHELX, *Acta Cryst.*, 2008, A64, 112-122, incorporated herein by reference in its entirety). The refinement and further calculations were carried out with SHELXL-2014 (G. M. Sheldrick, Crystal Refinement with SHELXL, *Acta Cryst.*, 2015, C71, 3-8, incorporated herein by reference in its entirety). The NH H atoms located in a Difference Fourier map were refined with a distance restraint of N—H=0.88(2) Å and H—H=1.40(2) Å. The C-bound H-atoms were included in calculated positions and treated as riding atoms: C—H=0.95-1.0 Å with U$_{iso}$(H)=1.5 U$_{eq}$(C) for methyl hydrogen atoms, and 1.2 U$_{eq}$(C) for other hydrogen atoms. The non-H atoms were refined anisotropically using weighted full-matrix least squares on F$^2$. A semi-empirical absorption correction was applied using the MULscanABS routine in PLATON (A. L. Spek, *Acta Cryst.*, 2009, D65, 148-155, incorporated herein by reference in its entirety). The crystal data and refinement details are given in Table 1. CCDC 1531011 and 1531012 for complexes (III) and (V) contain the supplementary crystallographic data for this disclosure, which can be obtained free of charge from The Cambridge Crystallographic Data Centre via www.ccdc.cam.ac.uk/data_request/cif.

TABLE 1

Crystal data and details of the structure refinement for complexes III and V

| Parameter | (III) | (V) |
|---|---|---|
| Empirical formula | C$_{32}$H$_{46}$AuF$_6$N$_4$PSe | C$_{32}$H$_{46}$AuF$_6$N$_4$PSe |
| Formula weight | 907.62 | 907.62 |
| CCDC number | 1531011 | 1531012 |
| Crystal system | Monoclinic | Monoclinic |
| Space group | P 21/c | P 12/n |
| a, b, c (Å) | 13.3698(6), 17.3635(5), 16.0631(6) | 10.7319(4), 26.0990(15), 12.5928(5) |
| α, β, γ (°) | 90, 102.411(3), 90 | 90, 92.543(3), 90 |
| V (Å$^3$) | 3641.8(2) | 3523.7(3) |
| Z | 4 | 4 |
| ρ$_{calc}$ (g cm$^{-3}$) | 1.655 | 1.711 |
| F(000) | 1792 | 1792 |
| Crystal size/mm | 0.13 × 0.31 × 0.40 | 0.19 × 0.30 × 0.42 |
| μ (mm$^{-1}$) | 5.141 | 5.313 |
| Temperature (K) | 173(2) | 173 |
| λ MoKα (Å) | 0.71073 | 0.71073 |
| 2 θ range (°) | 1.560-25.631 | 1.560-25.249 |
| h, k, l limits | −16:16, −21:19, −19:19 | −12:11, −31:31, −15:13 |
| Reflections: collected/Uniq. | 41663/6862 (R$_{int}$ = 0.0217) | 29366/6353 (R$_{int}$ = 0.0706) |
| T$_{max}$, T$_{min}$ | 1.0000, 0.4115 | 1.0000, 0.3218 |
| Data/restraints/parameters | 6862, 1, 490 | 6353, 0, 417 |
| R[F$^2$ > 2σ(F$^2$)], wR(F$^2$), S | 0.0183, 0.0419, 1.009 | 0.0591, 0.1058, 1.002 |
| Δρ$_{max}$, Δρ$_{min}$ (e Å$^{-3}$) | 0.677, −0.577 | 1.834, −2.789 |

EXAMPLE 3

Synthesis of Gold(I) Complexes (II-VI)

To 0.127 g (0.500 mmol) AgPF$_6$ in 5.0 mL ethanol was added 0.311 g (0.500 mmol) chlorido[1,3-Bis(2,6-diisopropylphenyl)imidazol-2-ylidene]gold(I), [Au(IPr)(Cl)] (complex 0) dissolved in 15.0 mL of CH$_2$Cl$_2$. After stirring for 5 minutes at room temperature, the solution was filtered. To the filtrate, 0.500 mmol selenone (1,3-imidazolidine-2-selenone (ligand 1) or its derivatives (ligands 2-5)) was added. The solution gas stirred for 1 hour, filtered and then kept in refrigerator for crystallization. After three to four days the products were separated. Complexes II, IV and VI were separated as white, gray, and yellow powdered solids, respectively. Complexes III and V were obtained as grayish, and white crystals, respectively.

EXAMPLE 4

Analytical and Spectroscopic Data

[Au(IPr)(ImSe)]PF$_6$ (II), Calc. for C$_{30}$H$_{42}$AuF$_6$PN$_4$Se, MW=879.57 g/mol: C, 40.97; H, 4.81; N, 6.37. Found: C, 41.38; H, 4.64; N, 6.28. Yield=0.248 g (56%). $^1$H NMR (CDCl$_3$, ppm): δ 8.85 (NH, s, 2H), 7.39 (C3-H, d, 2H), 7.57 (C4-H, t, 2H), 2.56 (C5-H, m, 4H), 1.33 (C6-H, d, 12H), 1.28 (C7-H, s, 12H), 7.65 (C8-H, s, 2H), 3.60 (C11-H, s, 4H). $^{13}$C NMR (CDCl$_3$, ppm): δ 145.1 C(1), 132.7 C(2), 123.2 C(3), 130.0 C(4), 27.8 C(5), 23.5 C(6), 23.0 C(7), 123.4 C(8), 181.6 C—Au, 168.7 C═Se, 44.8 C(11). $^{77}$Se NMR (CDCl$_3$, ppm): δ 42.80.

[Au(IPr)(EtImSe)]PF$_6$ (III), Calc. for C$_{32}$H$_{46}$AuF$_6$N$_4$PSe, MW=907.62 g/mol: C, 42.39; H, 5.11; N, 6.18. Found: C, 42.43; H, 5.83; N, 6.46. Yield=0.264 g (60%). $^1$H NMR (CDCl$_3$, ppm): δ 8.95 (NH, s, 1H), 7.36 (C3-H, d, 2H), 7.61 (C4-H, t, 2H), 2.54 (CS-H, m 4H), 1.31 (C6-H$_3$, d, 12H), 1.26 (C7-H, s, 12H), 7.33 (C8-H, s, 2H), 3.46 (C11-H, m, 2H), 3.54 (C12-H, m, 2H), 3.76 (C13-H, m, 2H), 1.15

(C14-H, m, 3H). $^{13}$C NMR (CDCl$_3$, ppm): δ 145.9 C(1), 133.5 C(2), 123.9 C(3), 131.3 C(4), 28.8 C(5), 24.4 C(6), 23.9 C(7), 124.4 C(8), 182.0 C—Au, 171.8 C=Se, 43.9 C(11), 49.0 C(12), 43.4 C(13), 12.0 C(14). $^{77}$Se NMR (CDCl$_3$, ppm): δ 75.36.

[Au(IPr)(PrImSe]PF$_6$ (IV), Calc. for C$_{33}$H$_{48}$AuF$_6$PN$_4$Se, MW=921.65 g/mol: C, 43.05; H, 5.25; N, 6.09. Found: C, 42.57; H, 5.51; N, 5.81. Yield=0.240 g (55%). $^1$H NMR (CDCl$_3$, ppm): δ 9.02 (NH, s, 1H), 7.38 (C3-H, d, 2H), 7.62 (C4-H, t, 2H), 2.55 (C5-H, m, 4H), 1.31 (C6-H, d, 12H), 1.26 (C7-H, s, 12H), 7.37 (C8-H, s, 2H), 3.76 (C11-H$_2$, t, 2H), 3.48 (C12-H, t, 2H), 3.28 (C13-H, t, 2H), 1.56 (C14-H, m, 2H), 0.86 (C15-H, t, 3H). $^{13}$C NMR (CDCl$_3$, ppm): δ 146.0 C(1), 133.5 C(2), 123.9 C(3), 131.2 C(4), 28.8 C(5), 24.5 C(6), 23.9 C(7), 124.4 C(8), 182.4 C=Au, 170.5 C=Se, 43.6 C(11), 49.7 C(12), 50.7 C(13), 20.2 C(14), 10.9 C(15). $^{77}$Se NMR (CDCl$_3$, ppm) δ 79.40.

[Au(IPr)(Me$_2$ImSe]PF$_6$ (V), Calc. for C$_{32}$H$_{46}$AuF$_6$PN$_4$Se, MW=907.63 g/mol: C, 42.39; H, 5.11; N, 6.18. Found: C, 42.68; H, 5.21; N 5.91. Yield=0.265 g (60%). $^1$H NMR (CDCl$_3$, ppm): δ 8.92 (C3-H, d, 2H), 7.59 (C4-H, t, 2H), 2.51 (C5-H, m, 4H), 1.26 (C6-H, d, 12H), 1.25 (C7-H, s, 12H), 7.30 (C8-H, s, 2H), 3.55 (C11-H, s, 2H), 2.85 (C12-H, s, 6H). $^{13}$C NMR (CDCl$_3$, ppm): δ 141.7 C(1), 133.3 C(2), 123.7 C(3), 131.2 C(4), 28.8 C(5), 24.4 C(6), 23.9 C(7), 123.7 C(8), 181.3 C=Au, 170.4 C=Se, 49.9 C(11), 36.5 C(12). $^{77}$Se NMR (CDCl$_3$, ppm): δ 88.44.

[Au(IPr)(Et$_2$ImSe]PF$_6$ (VI), Calc. for C$_{34}$H$_{50}$AuF$_6$PN$_4$Se, MW=935.68 g/mol: C, 43.64; H, 5.39; N, 5.99. Found: C, 43.19; H, 5.71; N, 5.49. Yield=0.284 g (61%). $^1$H NMR (CDCl$_3$, ppm): δ 7.41 (C3-H, d, 2H); 7.61 (C4-H, t, 2H), 2.51 (C5-H, m, 4H), 1.31 (C6-H, d, 12H), 1.25 (C7-H, d, 12H), 7.31 (C8-H, s, 2H), 3.49 (C11-H, d, 2H); 3.75 (C12-H$_2$, t, 2H), 1.23 (C13-H, dd, 2H). $^{13}$C NMR (CDCl$_3$, ppm): δ 145.6 C(1), 133.5 C(2), 123.9 C(3), 131.1 C(4), 28.8 C(5), 24.5 C(6), 23.9 C(7), 124.4 C(8), 182.2 C=Au, 167.2 C=Se, 44.2 C(11), 47.0 C(12), 12.0 C(13). $^{77}$Se NMR (CDCl$_3$, ppm): δ 101.43.

EXAMPLE 5

Spectroscopic Characterization and Analysis

Complexes (II)-(VI) were prepared according to FIG. 1. The IR frequencies of the free ligands 1-5 and their gold(I) complexes (II)-(VI) are summarized in Table 2. The ν(C=Se) absorption band of the selenones observed in the range of 578-636 cm$^{-1}$ is decreased to lower a frequency in the range of 554-557 cm$^{-1}$ upon complexation. This significant shift demonstrates the formation of these complexes. On the other hand, the ν(N—H) stretching band is shifted towards a higher frequency region in the formed complexes relative to free ligands. This shift may be related to an increase in the π character of the C—N bond upon complexation. Similar shifts have been observed for other gold(I) complexes of selenones (S. Ahmad, A. A. Isab, A. R. Al-Arfaj and A. P. Arnold, Polyhedron, 2002, 21, 2099-2105; A. Ahmad and A. A. Isab, Trans. Met. Chem., 2003, 28, 540-543; and A. A. Isab, S. Ahmad and A. P. Arnold, Trans. Met. Chem., 2004, 29, 870-873, each incorporated herein by reference in their entirety).

TABLE 2

Selected IR frequencies (cm$^{-1}$) of the selenone ligands (1-5) and their gold(I) complexes (II)-(VI)

| Ligand/Complex | ν(C = Se) | ν(N—H) | ν(C—H) |
|---|---|---|---|
| [Au(IPr)Cl] 0 | — | — | 3073, 2960 |
| Ligand 1 | 585 | 3250 | — |
| (II) | 559 | 3382 | 3161, 2960 |
| Ligand 2 | 588 | 3198 | 2961 |
| (III) | 556 | 3396 | 3166, 2956 |
| Ligand 3 | 595 | 3210 | 2962 |
| (IV) | 557 | 3400 | 2960, 2871 |
| Ligand 4 | 636 | — | — |
| (V) | 556 | — | 2965, 2870 |
| Ligand 5 | 626 | — | — |
| (VI) | 556 | — | 3145, 2963, 2873 |

According to $^1$H and $^{13}$C solution-state NMR spectral data, values for precursor [Au(IPr)Cl] agree well with the previously reported literature (M. R. Fructos, T. R. Belderrain, P. de Fremont, N. M. Scott, S. P. Nolan, M. M. Diaz-Requejo and P. J. Perez, Angew. Chem. Int. Ed., 2005, 44, 5284-5288, incorporated herein by reference in its entirety). In $^1$H NMR, the N—H signals for selenones shift more downfield upon complexation compared to those of free ligands. The deshielding effect is related to an increase in the π character of the C—N bond due to the flow of electron density from nitrogen towards selenium upon coordination. In $^{13}$C NMR, chemical shifts of carbenic (C=Au) and C=Se carbon atoms of selenones are given in Table 3. The carbene carbon resonance is shifted downfield by more than 6 ppm with respect to its chemical shift in the precursor complex 0, [Au(IPr)Cl]. The downfield shift is consistent with the transfer of electron density from carbon to the metal atom upon coordination. Other resonances of the IPr ligand remain almost unaffected. On the other hand, C=Se resonances in gold(I) complexes II-VI appeared higher upfield by more than 6 ppm compared to those uncoordinated selenones. This trend of upfield shift is in accordance with the previously published literature data (M. I. M. Wazeer, A. A. Isab and S. Ahmad, J. Coord. Chem., 2005, 58, 391-398, incorporated herein by reference in its entirety).

TABLE 3

$^{13}$C NMR chemical shifts (ppm) for free ligands and gold(I) complexes (II)-(VI) in CDCl$_3$

| Ligand/complex | Au = C | C = Se |
|---|---|---|
| [Au(IPr)Cl] 0 | 175.3 | — |
| Ligand 1 | — | 175.8 |
| (II) | 181.6 | 168.7 |
| Ligand 2 | — | 178.7 |
| (III) | 182.0 | 171.8 |
| Ligand 3 | — | 179.6 |
| (IV) | 182.4 | 170.5 |
| Ligand 4 | — | 181.2 |
| (V) | 181.3 | 170.4 |
| Ligand 5 | — | 179.3 |
| (VI) | 182.2 | 167.2 |

$^{77}$Se NMR chemical shifts of free ligands (1-5) and complexes (II)-(VI) are given in Table 4. In $^{77}$Se NMR, an upfield shift of 5.5-30.7 ppm was observed for all the ligands upon complexation. The upheld shift is related to the binding of selenium to the metal atom. This observation is consistent with the data of previous studies (A. A. Isab, M. I. M. Wazeer, M. Fettouhi, S. Ahmad and W. Ashraf, Polyhedron, 2006, 25, 2629-2636; and A. O. S. Altoum, A. Alhoshani, K.

Alhosaini, M. Altaf, S. Ahmad, S. A. Popoola, A. A. Al-Saadi, A. A. Sulaiman and A. A. Isab, *J. Coord. Chem.*, 2017, 70, 1020-1031, each incorporated herein by reference in their entirety). The largest shift was observed for the ImSe complex (complex (II)). Since the scale of upfield shift may be directly related to the stability of the formed complexes, complex (II) formed by ImSe (ligand 1) may be the most stable among these complexes.

TABLE 4

$^{77}$Se NMR chemical shifts (ppm) for gold(I) complexes (II)-(VI) in CDCl$_3$.

| Compound | δ $^{77}$Se (ppm) | Δ |
|---|---|---|
| Ligand 1 | 73.53 | 30.73 |
| (II) | 42.80 | |
| Ligand 2 | 80.89 | 5.53 |
| (III) | 75.36 | |
| Ligand 3 | 85.50 | 6.10 |
| (IV) | 79.40 | |
| Ligand 4 | 101.00 | 12.56 |
| (V) | 88.44 | |
| Ligands | 114.10 | 12.67 |
| (VI) | 101.43 | |

Δ = δ(free ligand) − δ(complex)

Solid state $^{13}$C NMR chemical shifts of all complexes showed consistency with those in the solution state. This observation indicates that carbon atoms of gold(I) complexes in both solid and solution states experience similar chemical environments, and hence infers similar stabilities of the synthesized complexes in both solid and solution state. The $^{13}$C (MAS) NMR chemical shifts of complexes ((II)-(VI) and their precursor 0) are given in Table 5.

TABLE 5

$^{13}$C (MAS) Solid State NMR chemical shifts (ppm) for gold(I) complexes (II)-(VI) and their precursor 0).

| Ligand/complex | C1 | C2 | C3 | C4 | C5 | C6 | C7 | C8 | Au=C | C=Se | C11 | C12 | C13 | C14 | C15 |
|---|---|---|---|---|---|---|---|---|---|---|---|---|---|---|---|
| 0 | 145.5 | 133.9 | 123.0 | 130.7 | 28.7 | 24.4 | 24.0 | 124.2 | 175.3 | — | — | — | — | — | — |
| (II) | 145.1 | 132.7 | 123.2 | 130.0 | 27.8 | 23.5 | 23.0 | 123.4 | 181.6 | 168.7 | 44.9 | — | — | — | — |
| (III) | 144.8 | 133.1 | 122.1 | 131.4 | 28.0 | 24.1 | 22.1 | 125.1 | 184.6 | 169.5 | — | 48.6 br | 43.7 | 12.9 | — |
| (IV) | 147.4 | 134.4 | 123.8 | 131.8 | 30.3 | 25.5 | 23.5 | 124.7 | 188.5 | 171.5 | 45.2 | 50.0 | — | 20.3 | 12.6 |
| (V) | 144.9 | 135.2 | — | 132.6 br | 28.0 | 25.3 | 22.7 | 124.0 | 181.2 | 164.4 | 38.5 | 50.8 | — | — | — |
| (VI) | 146.6 | 133.5 | 124.7 | 131.7 | 30.1 | 24.8 | 23.1 | 126.8 | 186.3 | 166.6 | 45.2 | 52.2 | 13.3 | — | — |

EXAMPLE 6

Crystal Structure Description

Figure 2:
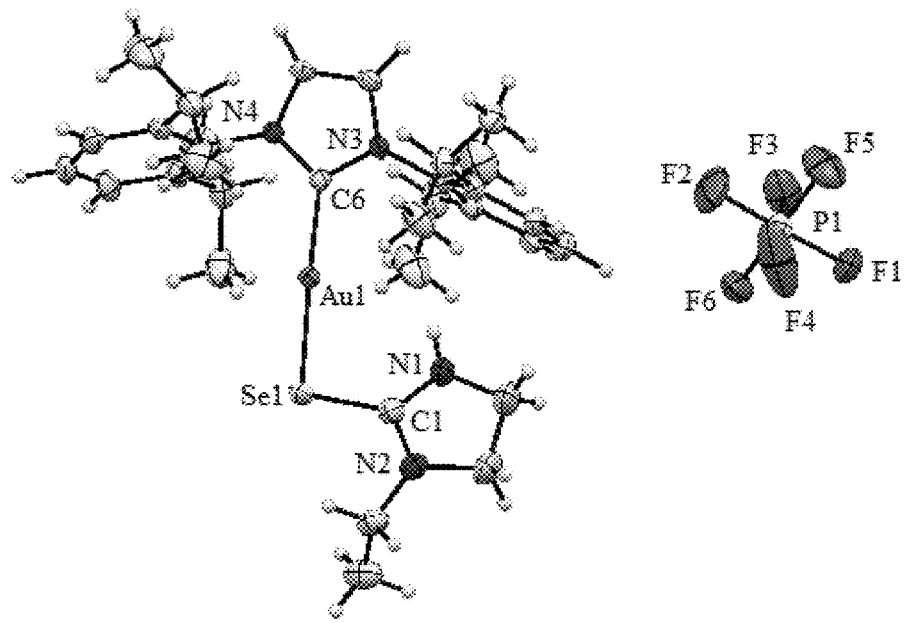
FIG. 2 is a view of ORTEP (Oak Ridge Thermal-Ellipsoid Plot Program) drawing (50% probability ellipsoids) of the crystal structure of gold(I) complex (III) with partial atom labelling.
Figure 3:
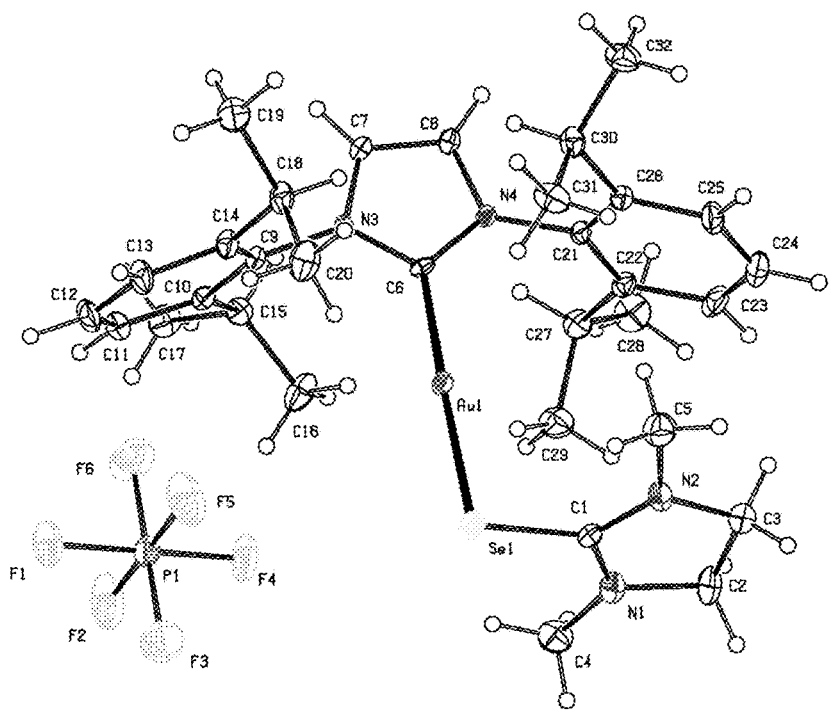
FIG. 3 is a view of ORTEP drawing (50% probability ellipsoids) of the crystal structure of gold(I) complex (V) with partial atom labelling.

Molecular structures of [Au(IPr)(EtImSe]PF$_6$ (III) and [Au(IPr)(Me$_2$ImSe]PF$_6$ (V) are depicted in FIGS. 2 and 3 respectively. The selected bond lengths and bond angles are given in Table 6. Both compounds were crystallized as ionic species consisting of [Au(IPr)(Selenone)]$^+$ and PF$_6^-$ ions. In the cationic complexes, the coordination geometry around the gold(I) ion is almost linear with C—Au—Se bonds having bond angles of 176.82(6)° and 176.76(17)° , for complexes (III) and (V), respectively. Compounds (III) and (V) are isostructural and possess similar bond parameters. Au—C and Au—Se bond lengths of both complexes are of the same magnitude as those found in other gold(i) compounds of carbene (T. J. Siciliano, M. C. Deblock, K. M. Hindi, S. Durmus, M. J. Panzner, C. A. Tessier and W. J. Youngs, *J. Organomet. Chem.*, 2011, 696, 1066-1071; B. Bertrand, L. Stefan, M. Pirrotta, D. Monchaud, E. Bodio, P. Richard, P. Le Gendre, E. Warmerdam, M. H. de Jager, G. M. M. Groothuis, M. Picquet and A. Casini, *Inorg. Chem.*, 2014, 53, 2296-2303; H. Sivaram, J. Tan and H. V. Huynh, *Organometallics*, 2012, 31, 5875-5883; B. K. Rana, A. Nandy, V. Bertolasi, C. W. Bielawski, K. D. Saha and J. Dinda, *Organometallics*, 2014, 33, 2544-2548; M. Altaf, M. Monim-ul-Mehboob, A. A. A. Seliman, A. A. Isab, V. Dhuna, G. Bhatia, and K. Dhuna, *Organomet. Chem.*, 2014, 765, 68-79; B. Bertrand, E. Bodio, P. Richard, M. Picquet, P. Le Gendre and A. Casini, *Organomet. Chem.*, 2015, 775, 124-129; M. V. Baker, P. J. Barnard, S. J. Berners-Price, S. K. Brayshaw, J. L. Hickey, B. W. Skelton, and A. H. White, *J. Organomet. Chem.*, 2005, 690, 5625-5635; R. Rubbiani, S. Can, I. Kitanovic, H. Alborzinia, Stefanopoulou, M. Kokoschka, S. Mönchgesang, W. S. Sheldrick, S. Wölfl and I. Ott, *J. Med. Chem.*, 2011, 54, 8646-8657; M. Z. Ghdhayeb, R. A. Hague and S. Budagumpi, *J. Organomet. Chem.*, 2014, 757, 42-50; and E. Deck, K. Reiter, W. Klopper and F. Breher, *Z. Anorg. Allg. Chem.*, 2016, 642, 1320-1328, each incorporated herein by reference in their entirety) and selenone (D. J. Nelson, F. Nahra, S. R. Patrick, D. B. Cordes, A. M. Z. Slawin and S. P. Nolan, *Organometallics*, 2014, 33, 3640-3645, incorporated herein by reference in its entirety) ligands. The bond connection around selenium atom is V-shaped (Au1—Se1—C1 95.30(2)° or 98.62(8)°), which is similar to what was observed previously (M. T. Aroz, M. C. Gimeno, M. Kulcsar, A. Laguna and. V. Lippolis, *Eur. J. Inorg. Chem.*, 2011, 2884-2894, incorporated herein by reference in its entirety). The bond angles around >C=Se and carbene carbon atoms represent a trigonal planar geometry. Similar to gold(I) complexes of IPr-based selenones, no evidence of aurophilic interactions was found in the crystal structures of complexes (III) and (V), presumably due to the steric bulkiness of the IPr and selenone groups. In complexes with smaller-sized ligands reported previously, such as [Me$_3$P—Au-Seu]$_2$Cl$_2$ (Me$_3$P=Trimethylphosphine, Seu=selenourea), the aurophilic interactions (Au—Au=3.0386(5) Å) favor the formation of a dinuclear complex (M. Fettouhi, M. I. M. Wazeer, S. Ahmad and A. A. Isab, *Polyhedron*, 2004, 23, 1-4). In the case of complex (II), the dimerization is probably hindered by the steric effect of the bulky ligands. The complex cations and PF$_6^-$ anions are associated to each other through electrostatic interactions.

TABLE 6

Selected bond distances (Å) and bond angles (°) for gold(I) complexes (III) and (V)

| Bond Distance | | Bond angles | |
|---|---|---|---|
| Complex (III) | | | |
| Au1—C6 | 2.009(2) | C6—Au1—Se1 | 176.82(6) |
| Au1—Se1 | 2.4030(3) | Au1—Se1—C1 | 98.61(8) |
| Se1—C1 | 1.868(3) | Au1—C6—N3 | 129.94(16) |
| N1—C1 | 1.328(3) | N3—C6—N4 | 105.46(19) |
| N1—C2 | 1.456(4) | N1—C1—N2 | 110.9(2) |
| N3—C6 | 1.339(3) | N1—C1—Se1 | 126.4(2) |

TABLE 6-continued

Selected bond distances (Å) and bond angles (°) for gold(I) complexes (III) and (V)

| Bond Distance | | Bond angles | |
|---|---|---|---|
| N3—C7 | 1.389(3) | N2—C1—Se1 | 122.68(19) |
| N3—C9 | 1.455(3) | C1—N1—C2 | 112.1(3) |
| | | C6—N3—C7 | 110.89(19) |
| Complex (V) | | | |
| Au1—C6 | 2.015(6) | C6—Au1—Se1 | 176.76(17) |
| Au1—Se1 | 2.4068(8) | Au1—Se1—C1 | 95.2(2) |
| Se1—C1 | 1.899(7) | Au1—C6—N3 | 129.3(5) |
| N1—C1 | 1.327(10) | N3—C6—N4 | 105.2(5) |
| N1—C2 | 1.469(10) | N1—C1—N2 | 111.9(7) |
| N3—C6 | 1.355(8) | N1—C1—Se1 | 124.0(6) |
| N3—C7 | 1.386(8) | N2—C1—Se1 | 124.0(6) |
| N3—C9 | 1.465(8) | C1—N1—C2 | 110.4(7) |
| | | C6—N3—C7 | 110.5(5) |

EXAMPLE 7

Measurement of Anticancer Activity

The cells were seeded at $3 \times 10^3$ cells/well in 100 μL of Dulbecco's Modified Eagle's Medium (DMEM) containing 10% fetal bovine serum (FBS) in a 96-well tissue culture plate and incubated for 72 h at 37° C., 5% $CO_2$ and 90% relative humidity in a $CO_2$ incubator. After incubation, 100 μL of 100, 50, 25 and 12.5 μM solutions of cisplatin and gold(I) complexes prepared in Dulbecco's Modified Eagle's Medium (DMEM) was each added to the cells and the cultures were incubated for 24 h. The medium in the wells was casted off, and 100 μL of DMEM containing MTT (0.5 mg/mL) was added to the wells, which were subsequently incubated in the $CO_2$ incubator at 37° C. in the dark for 4 h. After incubation, purple-colored formazan produced by the cells appeared as dark crystals in the bottom of the wells. The culture medium was carefully removed from each well to prevent disruption of the monolayer, and 100 μL of dimethyl sulfoxide (DMSO) was added in each well. The solution in the wells was thoroughly mixed to dissolve the formazan crystals which produced a purple solution. The absorbance of the 96 well-plates was measured at 570 nm with Labsystems Multiskan EX ELISA reader against a reagent blank. The experimental results were calculated as micro-molar concentration for 50% cell growth inhibition ($IC_{50}$) of each drug. The MTT assay was carried out in three independent experiments, each in triplicate.

EXAMPLE 8

In Vitro Cytotoxic Activities of Gold(I) Complexes (II-VI, and Precursor 0)

Figure 4:
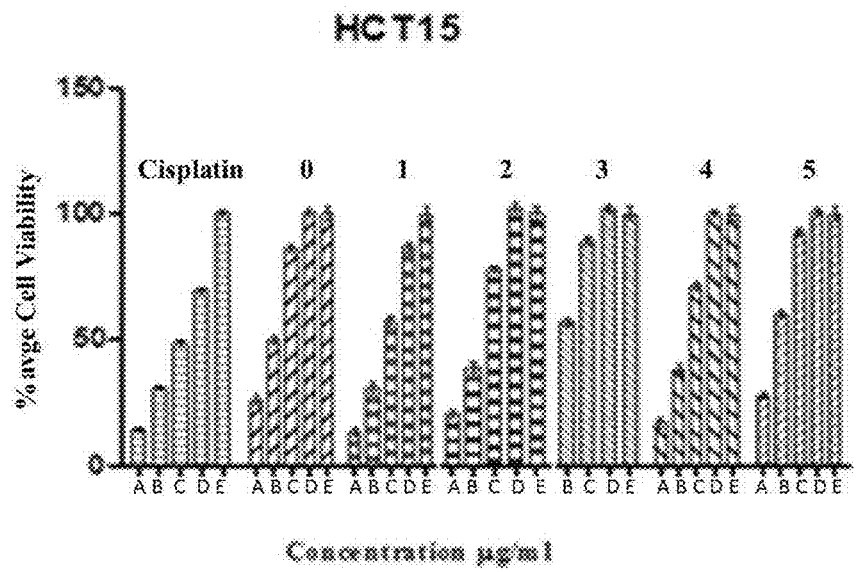
FIG. 4 is a bar graph showing the concentration dependent in vitro cytotoxicity of cisplatin and gold(I) complexes (II-VI) on the viability of HCT15 cancer cells.
Figure 5:
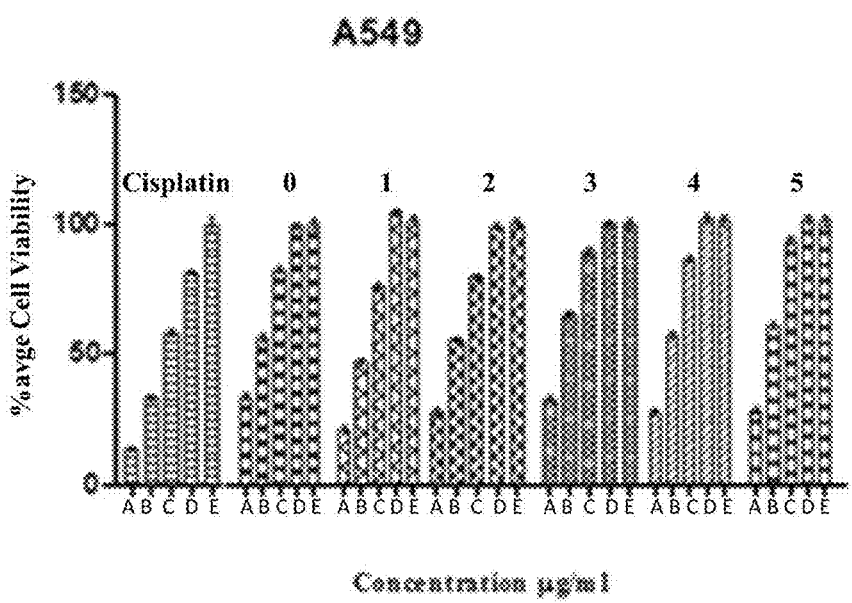
FIG. 5 is a bar graph showing the concentration dependent in vitro cytotoxicity of cisplatin and gold(I) complexes (II-VI) on the viability of A549 cancer cells.
Figure 6:
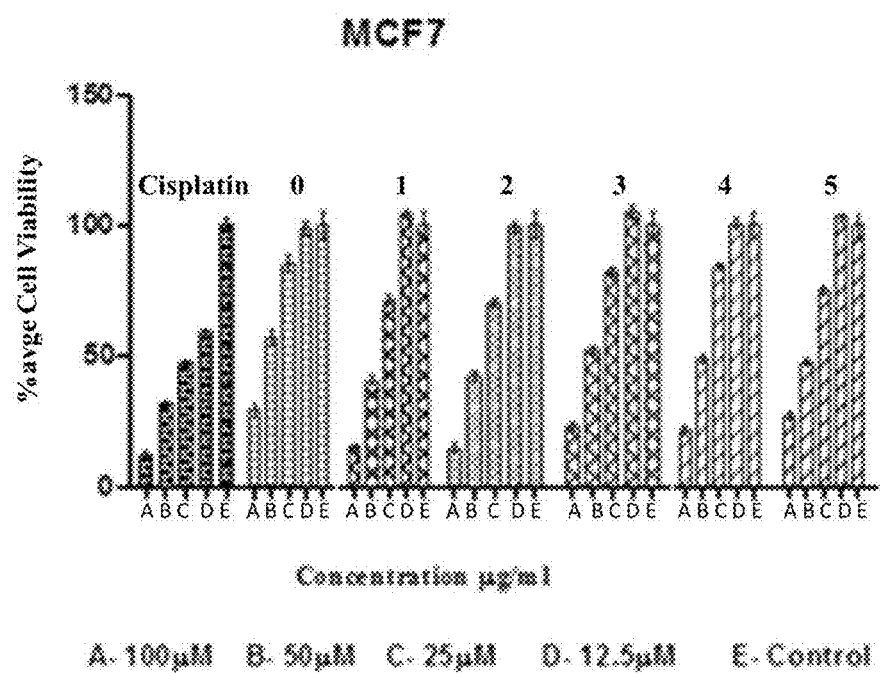
FIG. 6 is a bar graph showing the concentration dependent in vitro cytotoxicity of cisplatin and gold(I) complexes (II-VI) on the viability of MCF7 cancer cells.

Gold(I) complexes (II)-(VI) and precursor 0 were tested for in vitro cytotoxicity against A549 (human lung carcinoma). MCF7 (human breast adenocarcinoma), and HCT15 (human colon cancer) cell lines using MTT assay. Their activity was compared with the standard anticancer drug, cisplatin. The dose-dependent inhibition of cell proliferation was obtained by a specific increase in concentration of cisplatin and complexes (II-VI, and precursor 0) against a fixed number of three human cancer cell lines as shown in FIGS. 4-6. The $IC_{50}$ values (μM) of cisplatin, complexes (II)-(VI), and precursor 0 against cancer cell lines HCT15, A549 and MCF7 are shown in Table 7. The data show that the complex (II) is the most effective in inhibiting the growth of cancer cells. Its antiproliferative activity against HCT15 cells ($IC_{50}=33\pm1$ μM) is almost equal to that of cisplatin ($IC_{50}=33\pm2$ μM). All other studied gold complexes exhibit higher $IC_{50}$ values and are therefore, less effective than cisplatin in inhibiting the growth of cancer cells. The poor activity of these complexes may be related to a strong binding between IPr and selenone ligands as well as their steric bulkiness.

TABLE 7

$IC_{50}$ values (μM) of gold(I) complexes (II)-(VI) and precursor 0 against HCT15, A549, and MCF7 cancer cell lines.

| Complex | HCT15 | A549 | MCF7 |
|---|---|---|---|
| Cisplatin | 32 ± 2 | 42 ± 2 | 23 ± 4 |
| 0 | 122 ± 1 | 180 ± 2 | 110 ± 2 |
| (II) | 33 ± 1 | 47 ± 1 | 43 ± 2 |
| (III) | 45 ± 1 | 56 ± 1 | 42 ± 1 |
| (IV) | 62 ± 1 | 75 ± 1 | 53 ± 1 |
| (V) | 42 ± 1 | 58 ± 1 | 51 ± 1 |
| (VI) | 51 ± 2 | 71 ± 1 | 51 ± 1 |

EXAMPLE 9

Docking Studies of the Gold Complexes with Thioredoxin Reductase

The inhibition of thyroxine (TrX) is an important mechanism for chemotherapeutic treatment, especially with the use of gold and platinum complexes. However, selenium has also proved to be useful in cancer treatment (M. Selenius, A. K. Rundlof, E. Olm, A. P. Fernandes and M. Bjornstedt, *Antioxid. Redox Signal.* 2010, 12, 867-880; and S. Urig and K. Becker, *Semin. Cancer Biol.*, 2006, 16, 452-465, each incorporated herein by reference in their entirety). Hence, docking the synthesized gold(I) complexes which all contain selenium with a target protein human thioredoxin reductase was chosen (PDB ID: 3QFA) (K. Fritz-Wolf, S. Kehr, M. Stumpf, S. Rahlfs and K. Becker, *Nat. Commun.*, 2011, 2, 383-383, incorporated herein by reference in its entirety). The protein was validated using the Ramachandran plot with Moleman 2 to check for the percentage outlier. For a valid protein the percentage outlier should be within the range of 0 to 5% (G. J. Kleywegt, and T. A. Jones, *Structure*, 1996, 4, 1395-1400, incorporated herein by reference in its entirety). The target protein proved to be valid by having a percentage outlier of 3.1%. The docking results of the gold(I) complexes (II)-(VI) with human thioredoxin reductase are shown in Table 8.

TABLE 8

The docking results of gold(I) complexes (II)-(VI) with human thioredoxin reductase-thioredoxin

| Compound | Molecular mass | HBD | HBA | cLogP | Rotatable bonds | Binding Score | Ro5 violation |
|---|---|---|---|---|---|---|---|
| (II) | 735.6 | 2 | 4 | 7.05 | 8 | −75.40 | 2 |
| (III) | 763.7 | 1 | 4 | 6.87 | 9 | −70.80 | 2 |
| (IV) | 777.7 | 1 | 4 | 8.41 | 10 | −64.30 | 2 |
| (V) | 763.7 | 1 | 4 | 7.67 | 8 | −68.55 | 2 |
| (VI) | 791.7 | 1 | 4 | 8.84 | 10 | −69.52 | 2 |

The CLC drug discovery workbench (B. Li, S. Turuvekere, M. Agrawal, D. La, K. Ramani and D. Kihara, *Proteins*, 2008, 71, 670-683, incorporated herein by reference in its entirety) program was used to dock the gold complexes to the target protein, thioredoxin reductase (PDB ID: 3QFA). However, the initial ligands were extracted from the target protein before being docked with the gold complexes. The find binding pocket tool was used to find the druggable sites within the target protein based on Li et al's principle (A. C. Cheng, R. G. Coleman, K. T. Smyth, Q. Cao, P. Soulard, D. R. Caffrey, A. C. Salzberg and E. S. Huang, *Nat. Biotechnol.*, 2007, 25, 71-75, incorporated herein by reference in its entirety) that most of the druggable sites are within the largest solvent-accessible pockets found in a protein. Also, good drug-binding pockets are often condensed (B. Knudsen and K. Thomas, *CLC Drug Discovery Workbench User Manual*, 2016, 1-367, incorporated herein by reference in its entirety). The find bind pocket tool gave a druggable binding site which had a volume of about 4000 Å$^3$. The complexes were docked to the target protein with a binding site with a radius of 15 Å. This was chosen to ensure that the binding site covered the maximum possible part of the target protein. The docking result of the gold(I) complexes (II-VI) with the target protein is depicted in Table 8.

Figure 7A:
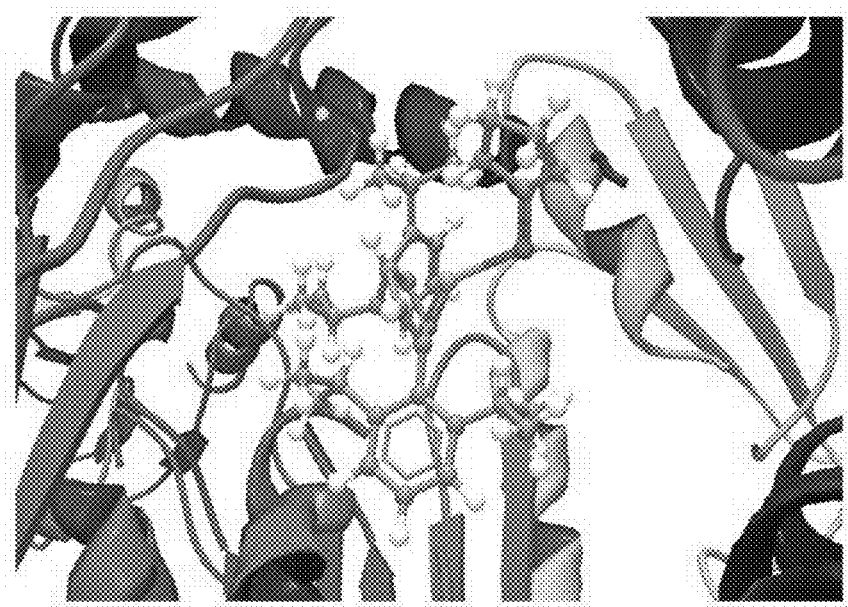
FIG. 7A shows the docking conformation of gold(I) complex (II) in the binding site of thioredoxin reductase.
Figure 7B:
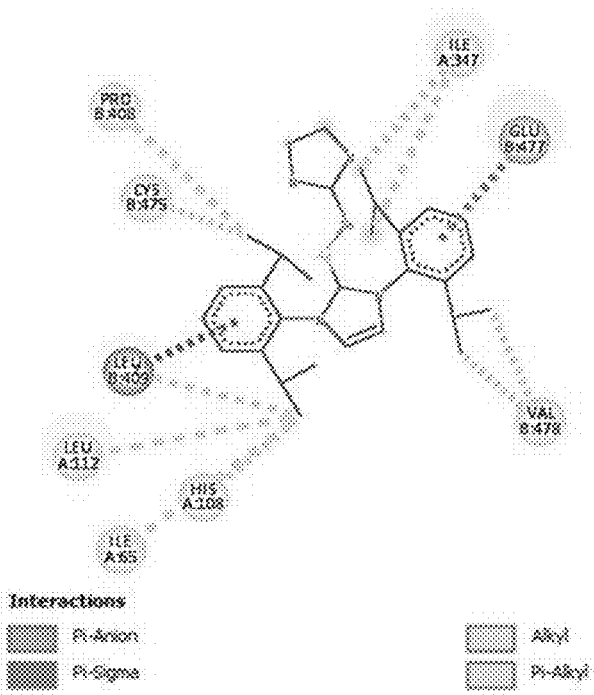
FIG. 7B shows the molecular interactions of gold(I) complex (II) with the amino acids in thioredoxin.
Figure 8A:
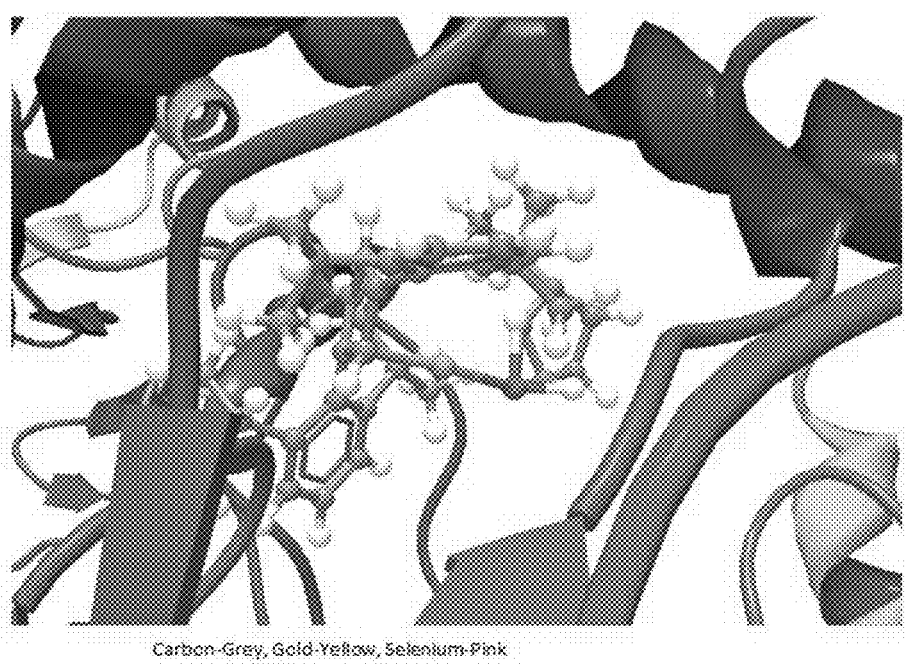
FIG. 8A shows the docking confirmation of gold(I) complex (III) in the binding site of thioredoxin reductase.
Figure 8B:
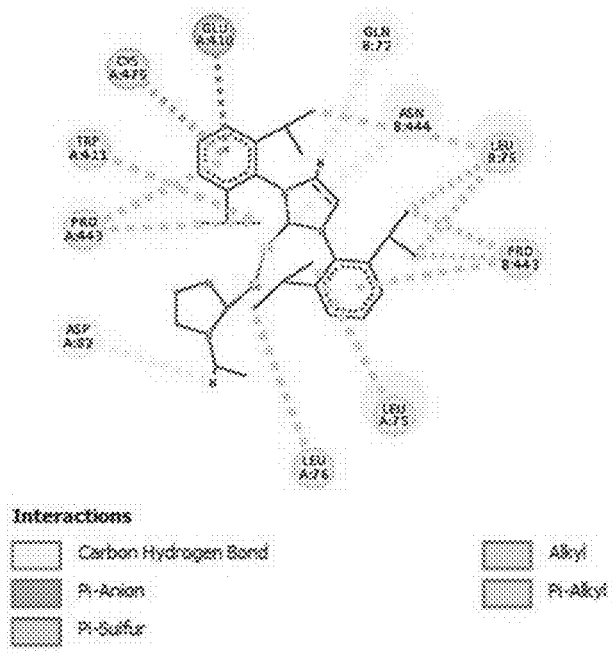
FIG. 8B shows the molecular interactions of gold(I) complex (III) with the amino acids in thioredoxin.
Figure 9A:
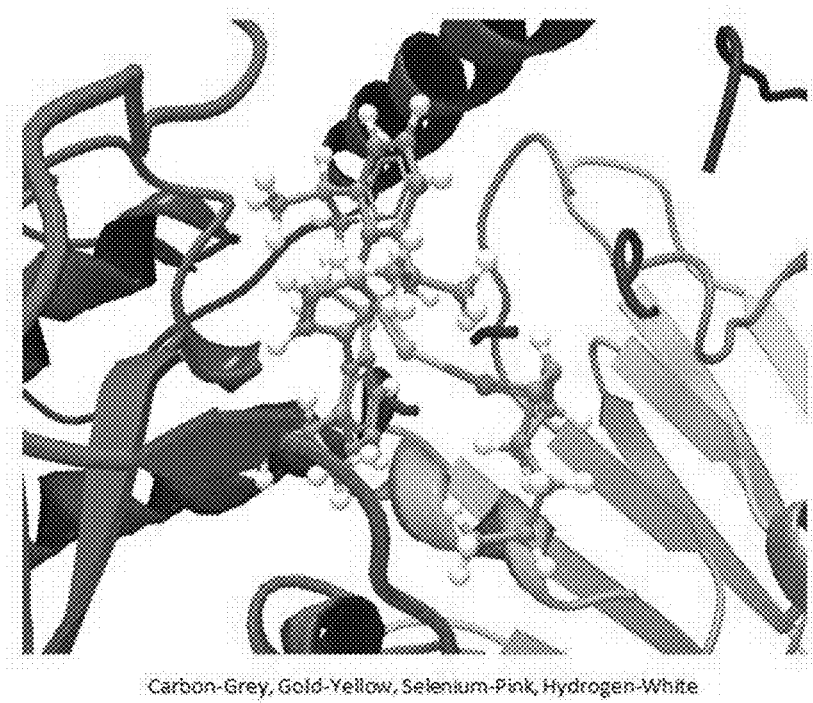
FIG. 9A shows the docking conformation of gold(I) complex (IV) in the binding site of thioredoxin reductase.
Figure 9B:
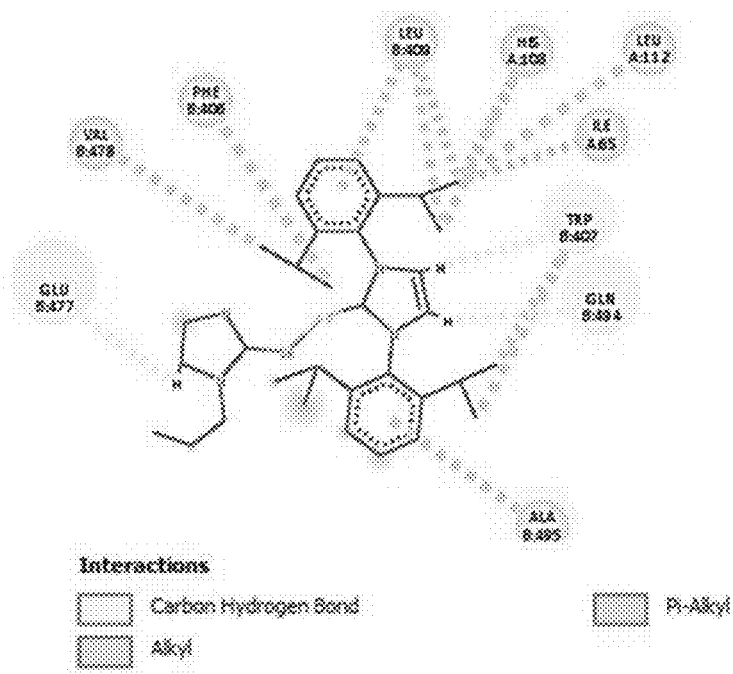
FIG. 9B shows the molecular interactions of gold(I) complex (IV) with the amino acids in thioredoxin.
Figure 10A:
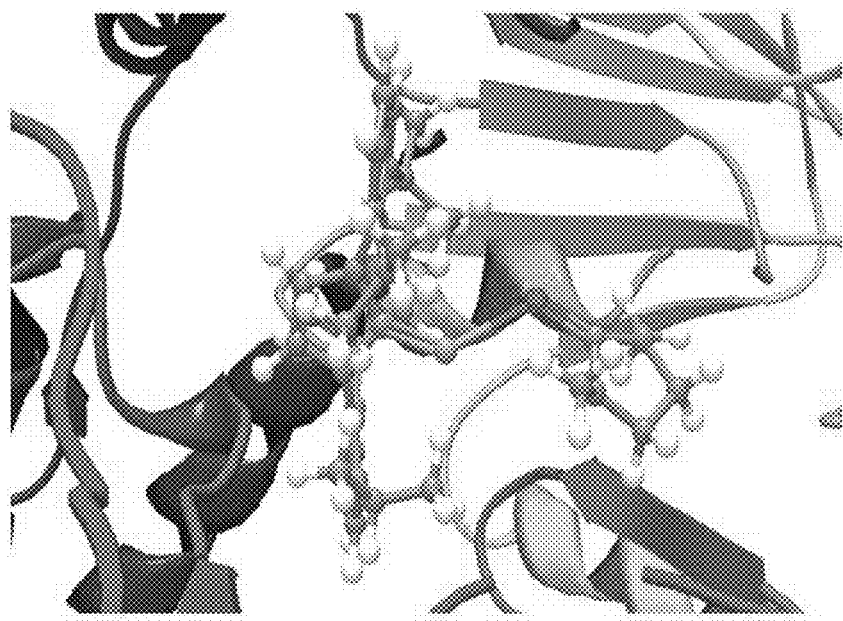
FIG. 10A shows the docking conformation of gold(I) complex (V) in the binding site of thioredoxin reductase.
Figure 10B:
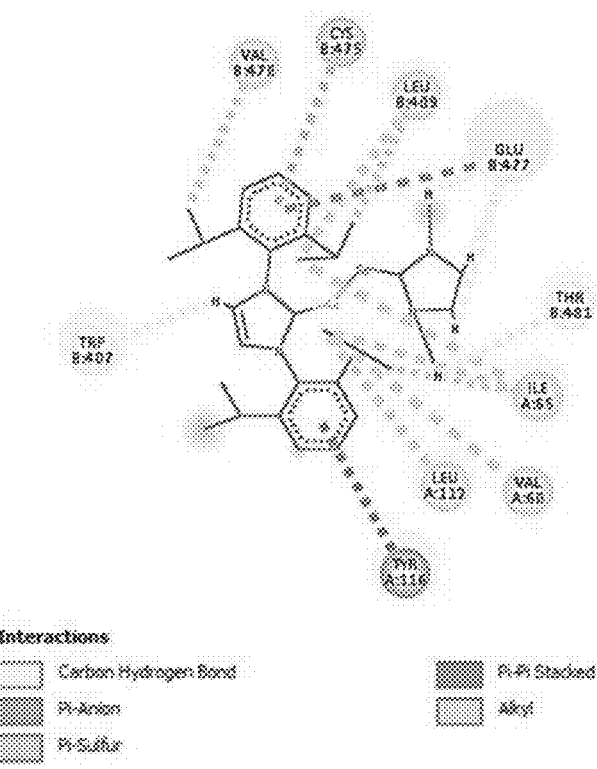
FIG. 10B shows the molecular interactions of gold(I) complex (V) with the amino acids in thioredoxin.
Figure 11A:
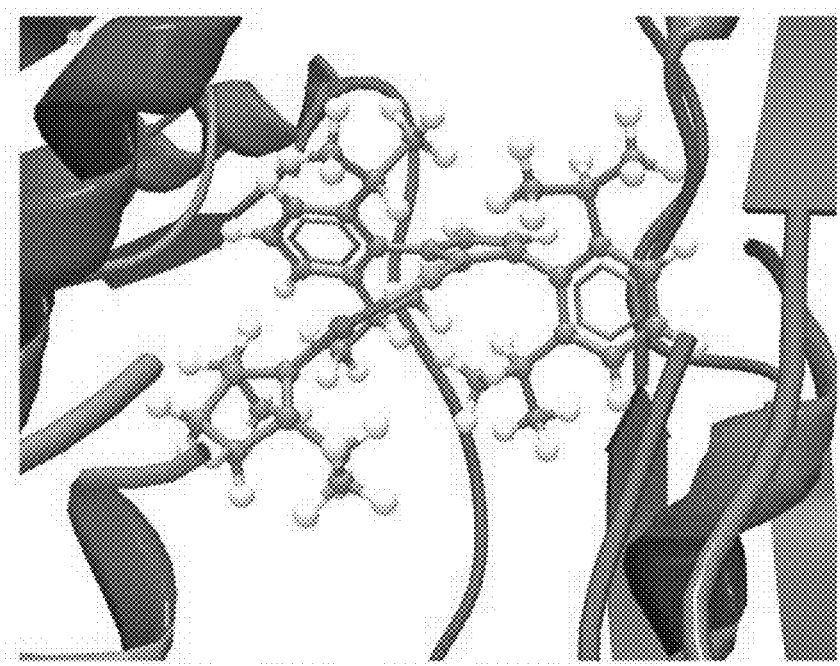
FIG. 11A shows the docking conformation of gold(I) complex (VI) in the binding site of thioredoxin reductase.
Figure 11B:
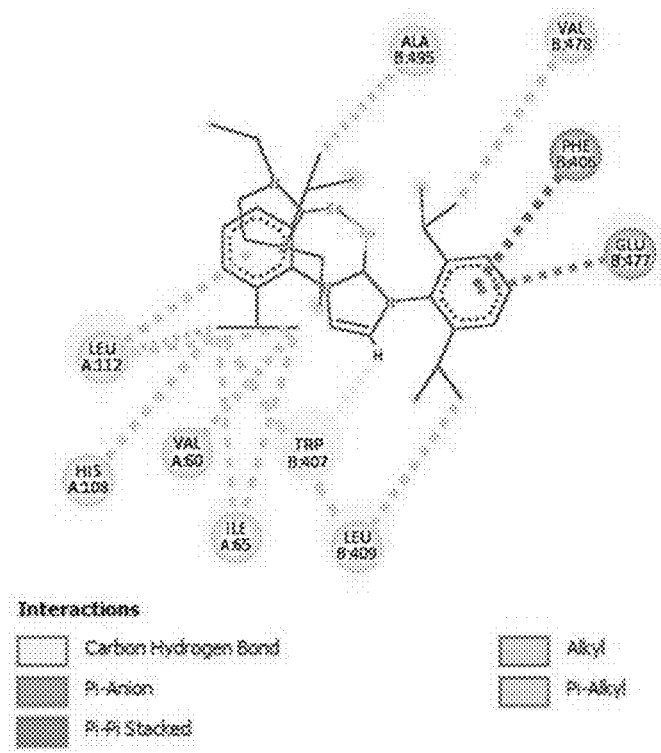
FIG. 11B shows the molecular interactions of gold(I) complex (VI) with the amino acids in thioredoxin.

All the complexes had a good binding affinity with the target protein with relatively high negative scores except for complex (IV) (−64.30) since the more negative a docking score, the better a binding affinity. Complex (II) scored the highest binding affinity (−75.27) and showed molecular interactions such as alkyl and pi-alkyl with the amino acids LEU 112, ILE 347, HIS 108, GLU 477, PRD 408, CYS 475, PHE 406 and VAL478 present in the target protein (FIGS. 7A and 7B). The molecular interactions of all the complexes (FIGS. 7A-11A, and 7B-11B) show some common amino acids which imply the complexes all have similar binding modes in the target protein. All the complexes violate the Lipinski's rule of five, by having a molecular mass and calculated logP (clogP) greater than 500 and 5, respectively. However, this does not deter them from being used as potential anticancer therapeutics since they can all be embodied in lead compounds (C. A. Lipinski, F. Lombardo, B. W. Dominy and P. J. Feeney, *Adv. Drug Deliv. Rev.*, 2001, 46, 3-26; and C. A. Lipinski, *Adv. Drug. Deliv. Rev.*, 2016, 101, 31-41, each incorporated herein by reference in their entirety).

The invention claimed is:

1. A gold(I) complex of Formula (I)

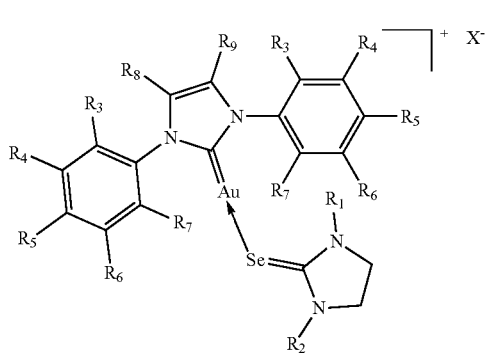

or a salt thereof, a solvate thereof, a tautomer thereof, a stereoisomer thereof, or a mixture thereof;
wherein:
$R_1$ and $R_2$ are independently selected from the group consisting of a hydrogen, an optionally substituted alkyl, an optionally substituted cycloalkyl, and an optionally substituted arylalkyl;

$R_3$, $R_4$, $R_5$, $R_6$, and $R_7$ are independently selected from the group consisting of a hydrogen, an optionally substituted alkyl, an optionally substituted alkenyl, an optionally substituted alkynyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro;

$R_8$ and $R_9$ are independently a hydrogen, or an optionally substituted alkyl; and X is an anion.

2. The gold(I) complex of Formula (I) of claim 1, wherein the anion is a hexafluorophosphate ion, a trifluoromethanesulfonate ion, a tetrafluoroborate ion, a perchlorate ion, or a halide ion.

3. The gold(I) complex of Formula (I) of claim 1,
wherein $R_1$ and $R_2$ are independently a hydrogen or an optionally substituted $C_1$-$C_6$ alkyl;
$R_3$ and $R_7$ are an isopropyl;
$R_4$, $R_5$, $R_6$, $R_8$, and $R_9$ are a hydrogen; and
X is a hexafluorophosphate.

4. The gold(I) complex of claim 3, wherein $R_1$ and $R_2$ are independently selected from the group consisting of a hydrogen, a methyl, an ethyl, and a n-propyl.

5. The gold(I) complex of claim 1, which is a compound selected from the group consisting of

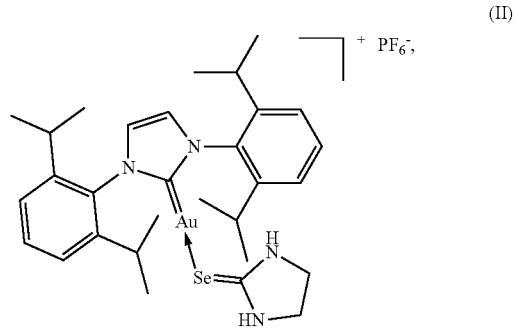

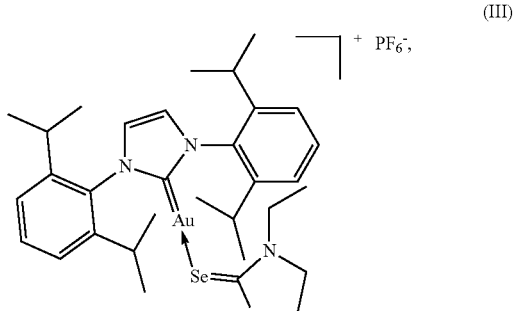

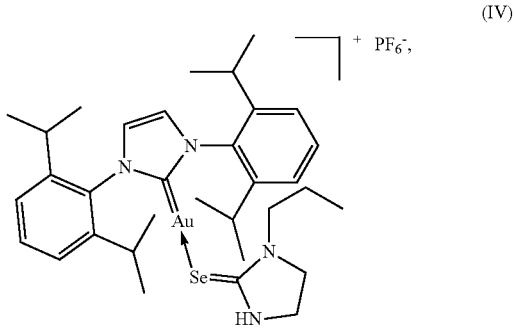

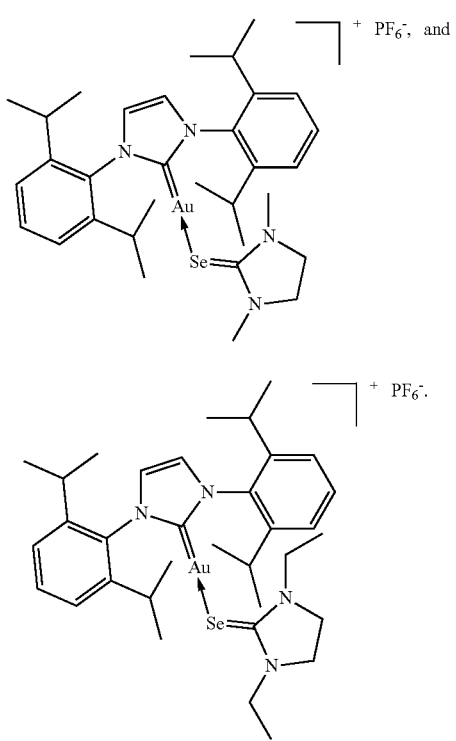

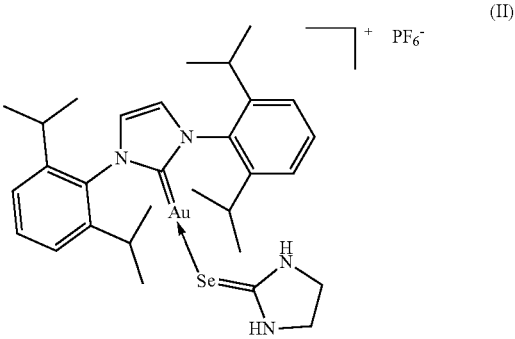

6. A pharmaceutical composition comprising:
the gold(I) complex of Formula (I) of claim 1; and
a pharmaceutically acceptable carrier and/or excipient.

7. The pharmaceutical composition of claim 6, which comprises 0.1-400 μM of the gold(I) complex relative to the total volume of the composition.

8. The pharmaceutical composition of claim 6, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

9. The pharmaceutical composition of claim 6, further comprising a chemotherapeutic agent.

10. The pharmaceutical composition of claim 6, wherein $R_1$ and $R_2$ are independently selected from the group consisting of a hydrogen, a methyl, an ethyl, and a n-propyl, $R_3$ and $R_7$ are an isopropyl, $R_4$, $R_5$, $R_6$, $R_8$, and $R_9$ are a hydrogen, and X is a hexafluorophosphate.

11. The pharmaceutical composition of claim 6, wherein the gold(I) complex is or a salt thereof, a solvate thereof, or a mixture thereof.

12. A method for treating a proliferative disorder, comprising administering the pharmaceutical composition of claim 6 to a subject in need of therapy.

13. The method of claim 12, wherein 1-300 mg/kg of the gold(I) complex of Formula (I) is administered per body weight of the subject.

14. The method of claim 12, wherein $R_1$ and $R_2$ are independently selected from the group consisting of a hydrogen, a methyl, an ethyl, and a n-propyl, $R_3$ and $R_7$ are an isopropyl, $R_4$, $R_5$, $R_6$, $R_8$, and $R_9$ are a hydrogen, and X is a hexafluorophosphate.

15. The method of claim 12, wherein the proliferative disorder is cancer.

16. The method of claim 15, wherein the cancer is at least one selected from the group consisting of colon cancer, breast cancer, and lung cancer.

17. The method of claim 15, wherein the cancer is resistant to at least one platinum-based chemotherapy drug.

18. The method of claim 16, wherein the cancer is colon cancer.

19. The method of claim 17, wherein the platinum-based chemotherapy drug is cisplatin.

20. The method of claim 12, wherein the subject is a mammal.

* * * * *